US012678122B2

(12) United States Patent
Slagmolen et al.

(10) Patent No.: US 12,678,122 B2
(45) Date of Patent: Jul. 14, 2026

(54) SYSTEM AND METHODS FOR CALIBRATION OF X-RAY IMAGES

(71) Applicant: Materialise NV, Leuven (BE)

(72) Inventors: Pieter Slagmolen, Leuven (BE);
Christophe Van Dijck, Leuven (BE);
Koen Engelborghs, Leuven (BE);
Andy Enefer, Leuven (BE)

(73) Assignee: Materialise N.V., Leuven (BE)

( * ) Notice: Subject to any disclaimer, the term of this patent is extended or adjusted under 35 U.S.C. 154(b) by 384 days.

(21) Appl. No.: 18/311,182

(22) Filed: May 2, 2023

(65) Prior Publication Data

US 2023/0263498 A1 Aug. 24, 2023

Related U.S. Application Data

(63) Continuation of application No. PCT/US2021/058330, filed on Nov. 5, 2021.

(Continued)

(51) Int. Cl.
*A61B 6/58* (2024.01)
*A61B 6/00* (2024.01)
(Continued)

(52) U.S. Cl.
CPC ............ *A61B 6/582* (2013.01); *A61B 6/5247* (2013.01); *A61B 6/5294* (2013.01); *G06T 7/60* (2013.01);
(Continued)

(58) Field of Classification Search
CPC ..... A61B 6/582; A61B 6/5247; A61B 6/5294; G06T 7/60; G06T 7/75; G06T 7/80;
(Continued)

(56) References Cited

U.S. PATENT DOCUMENTS

| | | | | |
|---|---|---|---|---|
| 2011/0255765 | A1* | 10/2011 | Carlson ................ | A61B 6/5247 |
| | | | | 378/4 |
| 2018/0206812 | A1 | 7/2018 | Trautwein et al. | |
| 2018/0360411 | A1* | 12/2018 | Abkai .................. | A61B 6/5247 |

FOREIGN PATENT DOCUMENTS

| | | |
|---|---|---|
| EP | 3685752 A1 | 7/2020 |
| WO | 2022099068 A1 | 5/2022 |

OTHER PUBLICATIONS

Ryo Kurazume et al., 3D reconstruction of a femoral shape using a parametric model and two 2D fluoroscopic images, Computer Vision and Image Understanding, vol. 113, Issue 2, 2009, pp. 202-211, ISSN 1077-3142, https://doi.org/10.1016/j.cviu.2008.08.012. (Year: 2009).*

(Continued)

*Primary Examiner* — Gregory A Morse
*Assistant Examiner* — Ronde Lee Miller
(74) *Attorney, Agent, or Firm* — Dinsmore & Shohl LLP

(57) ABSTRACT

Certain embodiments provide a system for calibrating an X-ray image. The system may receive an X-ray image of an anatomical part of a patient. The system may further receive a 3-D surface scan of a surface of the patient where the anatomical part is located. The system may derive a measurement correction to apply to measurements of the X-ray image based on the 3-D surface scan. The measurement correction may account for: an orientation of the patient with respect to the X-ray detector plate, a first distance between the patient and the detector plate, or a second distance between the patient and an X-ray source used to generate the X-ray image. The system may further determine a corrected measurement of the anatomical part based on the measurement correction and a measurement taken from the X-ray image.

21 Claims, 29 Drawing Sheets

Related U.S. Application Data

(60) Provisional application No. 63/110,624, filed on Nov. 6, 2020.

(51) Int. Cl.
*G06T 7/60* (2017.01)
*G06T 7/73* (2017.01)
*G06T 7/80* (2017.01)

(52) U.S. Cl.
CPC .................. *G06T 7/75* (2017.01); *G06T 7/80* (2017.01); *G06T 2207/10028* (2013.01); *G06T 2207/10116* (2013.01); *G06T 2207/30008* (2013.01); *G06T 2207/30052* (2013.01)

(58) Field of Classification Search
CPC . G06T 2207/10028; G06T 2207/10116; G06T 2207/30008; G06T 2207/30052; G06T 2200/24; G06T 7/73; G06T 2200/04
See application file for complete search history.

(56) References Cited

OTHER PUBLICATIONS

Kurtz, William B., John E. Slamin, and Scott W. Doody. "Bone preservation in a novel patient specific total knee replacement." Reconstructive Review 6.1 (2016). (Year: 2016).*

Nett, Brian. "Magnification and Blurring Effects for Radiographers and Radiologic Technologists (with Focal Spot Blur Formula) • How Radiology Works." How Radiology Works, How Radiology Works LLC, Jul. 10, 2022 (Year: 2022).*

Nett, Brian. "Magnification and Blurring Effects for Radiographers and Radiologic Technologists (with Focal Spot Blur Formula)." How Radiology Works, Jul. 9, 2020, web.archive.org/web/20210304153206/ (Year: 2020).*

European Patent Office, International Search Report for International Application No. PCT/US2021/058330, dated Feb. 11, 2022, 3 pages.

* cited by examiner

Patient thickness = STD - SPD

Point cloud (left) or mesh (right) representation of the 3-D surface scan (pelvic surface)

Projection 1

Projection 2

Reconstruction with different SLD

600

602b

602a

602c

605

602d

606b

606a

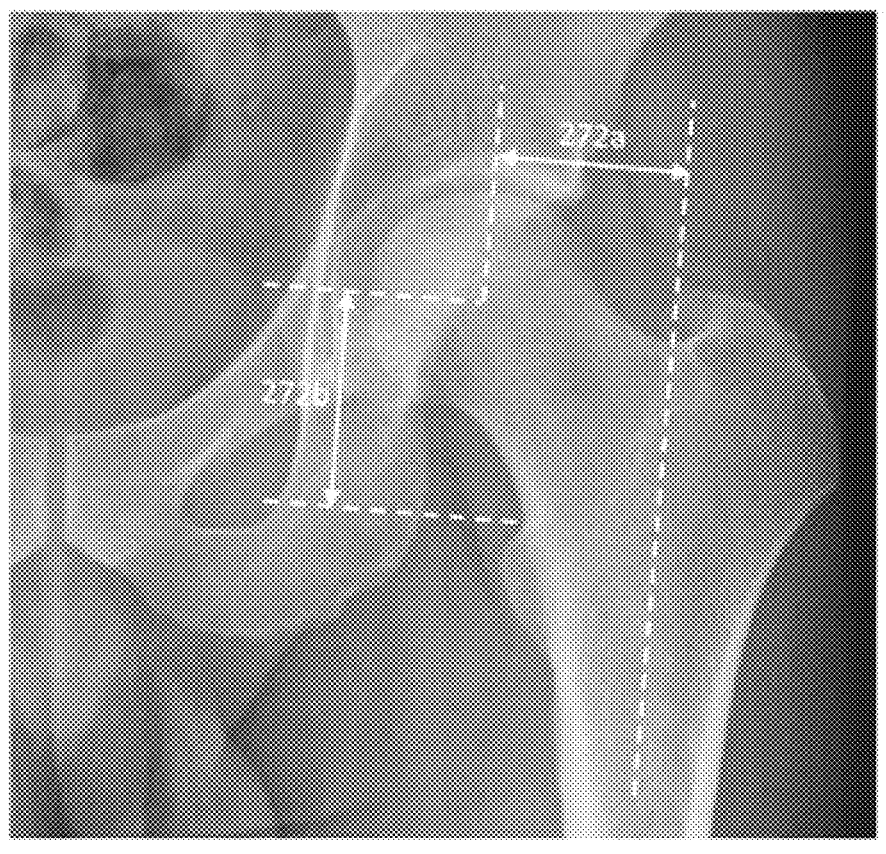
FIG. 27A
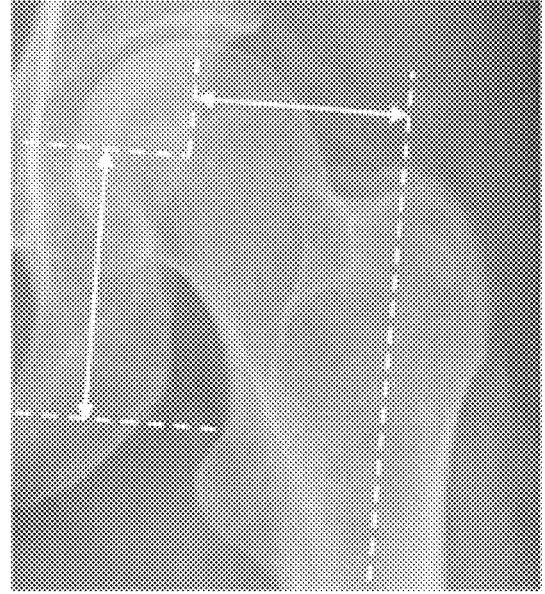
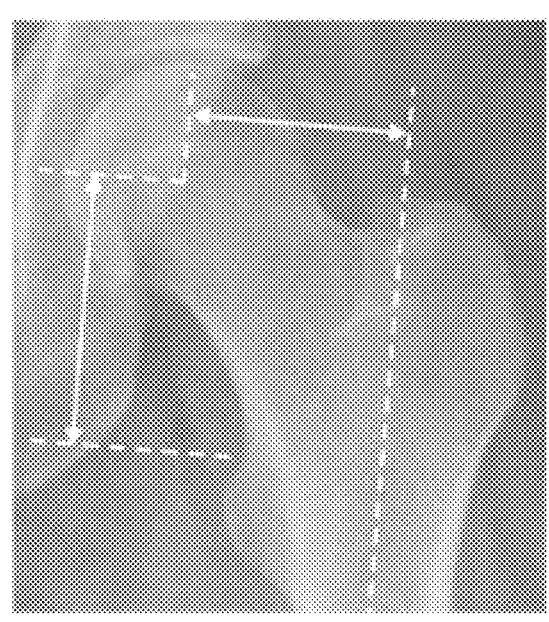
FIG 27B
FIG. 27C

SYSTEM AND METHODS FOR CALIBRATION OF X-RAY IMAGES

CROSS-REFERENCE TO RELATED APPLICATIONS

This application claims benefit of and priority to International Application No. PCT/US2021/058330 filed Nov. 5, 2021, which claims benefit of and priority to U.S. Provisional patent application Ser. No. 63/110,624 filed Nov. 6, 2020. The entire contents of each of these applications are incorporated herein by reference.

BACKGROUND OF THE INVENTION

Field of the Invention

This application relates to medical imaging. In some aspects, this application relates specifically to systems and methods for X-ray image calibration.

Description of the Related Technology

Digital templating may be used for performing pre-operative planning for orthopedic procedures based on X-ray images. A digital overlay of a 2-D representation of one or more of implant(s), implant component(s), screw(s), plate(s) or other surgical device(s) overlaid on a 2-D view of the bony anatomy of the patient on an X-ray image is performed. This allows the physician to pre-operatively assess the component sizing and placement, thus being better prepared for surgery.

The accuracy of measurements is critical for certain applications, such as for implant sizing. For example, an inaccurate femoral neck length measurement (e.g. due to a rotated leg during imaging), could lead to the implantation of an implant with an inappropriate femoral offset, which could lead to a limp, bony impingement or dislocation.

X-ray imaging is a flexible, versatile and readily available imaging modality. However, the setup, e.g., the relative positions of the X-ray source, the detector plate and the imaged subject, is not standardized. For example, the distance between the source and the detector plate can vary between machines and even between imaging sessions on one machine.

Additionally, the position of the X-ray source with respect to the center of the detector plate can be adjusted (e.g., the X-ray source can translate with respect to the detector plate), which means the X-ray is not always in front of the geometric center of the detector plate. Also, the distances from the subject to the detector plate and from the subject to the X-ray source is generally not known. Further, some machines perform imaging with a fixed X-ray source, other machines have a moving X-ray source. With a fixed X-ray source, the resulting image has parallax effects in both X (width) and Y (height) directions. This is often referred to as X-ray imaging with a point source. However, with a moving X-ray source, the resulting image has parallax effects in the X direction, but not in the Y direction. That is, with a moving X-ray source, objects are projected according to a perspective projection in the X direction, and according to a parallel projection in the Y direction. This is often referred to as X-ray imaging with a line source or linear source.

Machines may perform post-processing steps on the resulting images to compensate for some of these effects, but even these steps are not standardized.

Additionally, the patient's pose may vary. The location as well as the limb rotation of the patient in relation to the X-ray source and detector plate (e.g., digital imager) may vary, possibly also because of the patient's size and mobility restrictions related to his medical condition. Further, soft-tissue data cannot be easily obtained from X-ray scans.

Additionally and as illustrated in FIG. 1, a subject 2a positioned closer to the X-ray source 4 will appear larger in the image than an identical subject 2b standing closer to the detector plate 6. By looking at the projected image 8, one cannot conclusively determine the size of the imaged subject.

There are further artifacts: when the X-ray source 4 is close to the detector plate 6, parallax effects will be greater than when the X-ray source 4 is far away, because the X-rays come closer to being parallel when the X-ray source 4 is far away.

Finally, the proportions of a subject 2 cannot be reliably determined from an image 8, particularly with a moving X-ray source 4, as the height of the projection will be the height of the actual subject, but the width of the projection depends on how near or far the subject 2 is positioned from the detector plate 6.

To address the foregoing issues, an estimated scaling factor may be applied to the resulting 2-D image 8, which can adversely affect the accuracy of the planning procedure. Moreover, errors in patient's limb orientation are typically evaluated qualitatively by the surgeon when viewing the X-ray image 8, leading to a variable result that is hard to combine with more objective planning approaches.

For example and as illustrated in FIG. 2, an image 8a taken in preparation of a hip replacement ideally shows a frontal view of the patient's pelvis and femur (generally, anatomy 10). However, due to pain or lack of mobility, it is not always possible to put the patient 2 in the correct position. As a result, certain features of anatomy 10 or other visual features that the surgeon relies upon when planning the surgery, might appear differently in the 2-D image 8b (e.g. different shape, different proportions, different angle, different size). For example, if the pelvis is parallel to the detector plate 6, but the hip joint has internal or external rotation, the femoral neck will be depicted with foreshortening, and a neck length measurement will be incorrect. Some visual features might even appear in a different location. For example, if the patient 2 has a non-neutral pelvic tilt, the acetabular teardrop (a teardrop-shaped visual artifact resulting from the projections of sections of cortical wall from different parts of the pelvis that is often used as a reference during the planning of hip surgery) might look different, or may appear in a different place.

Thus, the impact of this unknown scaling is an important factor in most orthopedic procedures and particularly significant with pre-operative X-rays for joint replacement surgery. Furthermore, measurement(s) taken from the X-ray image 8 are affected by the 3-D to 2-D projection and so depend on the ability of the X-ray technician and the patient 2 to execute the imaging protocol which aims to position the patient's anatomy in an optimal way with respect to the plane of the X-ray detector plate 6 and the position of the X-ray source 4.

As set forth above, the uncertainty of measurements taken from an X-ray image 8 stem from both the scaling issue and the issue with patient positioning. Both result in measurements not being reliable.

In some cases, and as depicted in FIG. 3, the scaling may be corrected using a calibration marker 12, effectively an object with known geometry and size, which is attached to or positioned near the patient 2 during imaging. For example, the scaling object 2 may be a coin or a metal sphere of known diameter. The object geometry is incorporated in the software system used for digital templating and allows to determine the correct scaling factor for accurate measurements. The scaling factor is, for example, the known diameter of the calibration marker 12 divided by the diameter of the calibration marker 12 measured from the image 8.

However, the calibration marker 12 has a number of downsides. First, the imaging operator may forget to include the calibration marker 12 while scanning the patient 2. This occurs regularly as the majority of diagnostic X-ray imaging protocols do not require this kind of calibration.

Second, the calibration marker 12 should be attached in the right location for scaling, a location that may be determined by anatomical landmarks 14 of interest, e.g., on the bony anatomy 10 that may be difficult to identify in certain patients 2. Just like with the image 8 of the patient 2, the size of the calibration marker 12 in the image 8 will depend on the location of the calibration marker 12 with respect to the X-ray source 4 and detector plate 6, more particularly the distances between detector plate 6, calibration marker 12 and X-ray source 4. Therefore, a scaling factor deduced from that image 8 will only be relevant for depictions of anatomical features that lie at (substantially) the same distances from detector plate 6 and X-ray source 4. For example, if the surgeon is interested in measuring the femoral neck length, the calibration marker 12 should be placed at the same distance between the detector plate 6 and X-ray source 4 as the femoral neck. However, the radiologist needs to know that the femoral neck is what matters. Additionally, the femoral neck is not easily identifiable externally.

Third, the location where the calibration marker 12 is attached to or positioned near the patient 2 may vary. Likewise, attachment methods for attaching the calibration marker 12 to the patient 2 may also vary. For example, some calibration markers 12 are stuck to the patient 2 with tape or a stretchy belt, others are merely placed on the patient 2 (lying down or standing up), some need to be held in place by the patient 2, and some can be attached to the table by means of a long and flexible arm. Depending on the size of the patient 2, availability of attachment points may vary, which can be relevant for applications that require higher accuracy (e.g. hip arthroplasty). For example, if the patient 2 is very obese, it is possible that a calibration marker 12 placed at the side of the patient would fall out of the field of view. Furthermore, for more obese patients 12, making sure that the calibration marker 12 is in the same plane (relative to the X-ray source 4 and/or detector plate 6) as the anatomical region of interest is more difficult. Also, patient comfort (e.g. placement between legs) may drive the operator to place the calibration marker 12 in a suboptimal position.

Finally, the calibration marker 12 requires the user of the digital templating system to perform an additional step in the planning process, which adds time and a possible source of error. For example, a common way to calculate the scaling factor of a spherical calibration marker 12 is to draw a circle on the screen around the depiction of the marker in image 8, and then, from that circle, determine the diameter. Some planning software applications can identify the depiction of the calibration marker 12 automatically, others require the user to manually draw the outline. In either case, a complicating factor is that the image 8 of a sphere in an X-ray image never has a sharp edge, due to the diminishing travel length of the rays through the sphere as the rays approach the edge. An outline drawn in a low-contrast image 8 might result in a smaller circle than one drawn in a high-contrast image 8. Thus, error is introduced to the scaling factor (which results from the measurement taken from the depiction of the marker and the actual size of the marker) when the outline of the calibration marker 12 is drawn manually or the wrong size of the calibration marker 12 is input.

New technologies based on X-ray imaging allow predicting from one or more 2-D patient-specific images, a 3-D patient-specific shape (e.g., by using artificial intelligence (AI) or through fitting a 3-D population model, such as a statistical shape model, or another type of algorithm), thus extrapolating the patient-specific information to a 3-D representation of the anatomy. For example, EP3107477, which is hereby incorporated by reference, describes how a 3-D bone model can be reconstructed from one or more X-ray images 8, and a 3-D cartilage model can be reconstructed from the bone model. The reconstructed anatomical 3-D information can then be used for surgical planning and for the construction of surgical instruments such as guides or the creation of implants. To achieve an accurate 3-D representation, accurate calibration is again required.

In addition and as shown in FIGS. 4A-4D, when multiple X-ray images 8c, 8d of anatomical part 10 of patient 2 are used—for example, with different positions of the patient 2 or repositioning between image acquisitions of the X-ray source 4 and/or detector plate 6 by an operator or through a robotic system—each X-ray image 8 needs to be accurately scaled on a per-image basis. As shown in FIG. 4A, accurate scaling for each X-ray image 8c, 8d of anatomical part 10 is required so that a 3-D reconstruction based on the X-ray images 8c, 8d has the same sizes and proportions as the anatomical part 10 of the patient 2. Incorrect scaling may not only result in a 3-D reconstruction 10' of incorrect size (FIG. 4B) but also in a 3-D reconstruction 10" of incorrect proportions (FIG. 4C).

Further, the multiple X-ray images 8c, 8d need to be geometrically related to each other. In order to geometrically relate X-ray images 8 to each other, the main task is to determine their relative position in space, assuming the patient 2, or an imaged anatomical part 10 remains fixed in space. For example, if one X-ray machine is used, and first a frontal X-ray image 8c and then a lateral X-ray image 8d is taken of the patient's femur 10, both images are two different projections of the same femur. In reality the machine stays fixed and the femur 10 moves. For reconstructing the shape of the femur 10 from these two 2-D X-ray images 8c, 8d, however, it is easier to assume that the femur 10 stays fixed and the machine moves, or that multiple machines take images of the same femur 10 from different X-ray sources 4c, 4d towards different projection planes. In other words, both images 8c, 8d are taken, each with the corresponding X-ray source 4c, 4d in a particular position in the femur's 3-D coordinate system and with the corresponding detector plate 6c, 6d in a particular position and orientation in the femur's 3-D coordinate system. Each X-ray image 8c, 8d of the femur is defined by a particular projection. To correctly reconstruct a 3-D model of the anatomy of the femur from these 2-D projections, how the sources and projection planes of both are positioned in the single coordinate system of the femur must be understood. In other words, the positions of the X-ray sources 4c, 4d and projection planes of all X-ray images 8c, 8d must be expressed in a single coordinate system determined by the imaged subject. This may include a determination of the spatial relationship of both X-ray sources 4c, 4d and projection planes (e.g., surfaces of detector plates 6c, 6d) relative to each other. An incorrect spatial relationship between the X-ray images may lead to a 3-D reconstruction 10''' that has an incorrect shape and/or size (FIG. 4D).

As illustrated in FIG. 4E, a more elaborate 3-D calibration marker 12' can then be used from which the relative position of the X-ray data—e.g., the positions 12c', 12d' of the X-ray sources 4c, 4d and projection plane of the X-ray images 8c, 8d relative to the imaged subject 2— can be derived. The known size and shape of the elaborate calibration marker 12' should be such that its positions 12c', 12d' with respect to the X-ray sources 4c, 4d and detector plates 6c, 6d during imaging can be derived from its depiction in X-ray images 8c, 8d. X-ray images 8c, 8d can then be brought into a single coordinate system by making positions 12c', 12d' overlap. Depending on the shape of the elaborate calibration marker 12', specifics of the X-ray projection (e.g. X-ray source 4 to detector plate 6 distance (SDD), imaging direction, fixed versus moving source) may either be derived from the depictions of elaborate calibration marker 12' in X-ray images 8c, 8d, or may be taken as input. This process is sometimes referred to as registration of the X-ray image data. An example of such an elaborate calibration marker and the X-ray image data registration is disclosed in EP2704635, which is hereby incorporated by reference. Performing said reconstruction from 2-D imaging to 3-D models suffers from similar challenges as those seen with singular X-ray calibration for templating described above.

There is, therefore a need for improved systems and methods of calibrating X-ray images.

Recently, new technology has been introduced that allows to capture a 3-D surface with relatively low cost components. This technology (e.g., time-of-flight camera's, stereo reconstruction, etc.) has found its way into gaming, mixed-reality headsets or mobile devices such as tablets and smartphones. Even more recently, this technology has been added to medical imaging modalities such as CT (e.g., Siemens Somatom X.Cite) and X-ray imaging (Siemens YSIO X.Pree). Here, it operates as a tool to improve patient positioning, or scanning parameters.

It should be noted that the information included in the Background section herein is simply meant to provide a reference for the discussion of certain embodiments in the Detailed Description. None of the information included in this Background should be considered as an admission of prior art.

Summary of Embodiments of the Disclosure

In certain embodiments, based on the novel and inventive techniques discussed herein, the technology related to capturing a 3-D surface with relatively low cost components can be used to automatically calibrate or scale or register X-ray images for digital templating, for predicting 3-D anatomy avoiding the need for well positioned calibration markers (both standard and elaborate) or for combining the measured 3-D surfaces with 2-D information directly to make a surgical plan or instrument and for, subsequently, designing medical devices such as guides based on the gathered information and the surgical plan.

Certain embodiments provide techniques that combine one or more traditional X-ray images with a 3-D scan captured using a connected or add-on 3-D scanning system, e.g. a 3-D scanning system added onto, connected to or incorporated into an X-ray imaging system, or data derived from such 3-D scan such as an avatar representing the scanned anatomy location, for automatically scaling one or multiple X-rays or for registering them to achieve accurate digital templating or 3-D reconstruction or for providing extra quantitative or qualitative information on the relation between measurements taken from or visualized on the X-ray image and the corresponding 3-D measurements of the anatomy. From the same patient and at (approximately) the same time and position, both an X-ray image and 3-D scan are acquired. The location of the 3-D scanner in relation to the X-ray system is known (e.g., the 3-D scanning system is mounted in a known location with respect to the X-ray imaging system, or their relative position is calibrated with a known object, e.g. by 3-D scanning the known object as it is in a known position with respect to the X-ray imaging system). Based on this, the 3-D scan can be used to perform calibration of the X-ray image.

The 3-D scan itself will provide 3-D data relating to a surface of the patient and surrounding objects (such as the table he is lying on). This scan is typically represented as a point cloud or surface mesh.

The derived data could be a subdivision of the point cloud into separate surfaces such as the outline of the patient or the surface of the table. Derived data could also be a fitted 'generic' model, for example an avatar or a population model, such as a statistical shape model. This would allow to create a 3-D representation of the body outline of the patient, also for parts that aren't recorded with the 3-D scan (such as the back when lying on a table in a supine position).

The avatar could be a generic 3-D surface model (mesh) of a certain part of the anatomy (torso, lower legs, head, etc.). In some embodiments, this generic model could be an average representation of this part of the anatomy for a population. The avatar could be a multi-body 3-D surface model, with each body of the avatar representing a body part of a patient, and allowing (non-uniform) scaling of the different bodies and relative inter-body movements similar to natural movements between a patient's body parts, much like a virtual mannequin. In some embodiments, replacing the original 3-D scan of the patient with an avatar fitted to the 3-D scan may reduce the amount of data to be stored and handled in further processing steps. Moreover, it may remove details of the patient's anatomy that are irrelevant for the remaining medical diagnosis, treatment planning or treatment, thus enhancing patient privacy.

Certain embodiments provide a system for calibrating an X-ray image. The system may include a memory and a processor coupled to the memory. The processor may be configured to receive an X-ray image of an anatomical part of a patient. The processor may be further configured to receive a 3-D surface scan of a surface of a portion of the patient where the anatomical part is located. The processor may be further configured to derive a measurement correction to apply to measurements of the X-ray image based on the 3-D surface scan. The measurement correction accounts for at least one of: an orientation of the patient with respect to a detector plate used to capture the X-ray image when the X-ray image was captured, a first distance between the patient and the detector plate, or a second distance between the patient and an X-ray source used to generate the X-ray image when the X-ray image was captured. The processor may be further configured to determine a corrected measurement of the anatomical part based on the measurement correction and a measurement taken from the X-ray image.

Certain embodiments provide a method for calibrating an X-ray image. The method may include receiving an X-ray image of an anatomical part of a patient, and receiving a 3-D surface scan of a surface of a portion of the patient where the anatomical part is located. The method may further include deriving a measurement correction to apply to measurements of the X-ray image based on the 3-D surface scan, the measurement correction accounting for at least one of: an orientation of the patient with respect to a detector plate used to capture the X-ray image when the X-ray image was captured, a first distance between the patient and the detector plate, or a second distance between the patient and an X-ray source used to generate the X-ray image when the X-ray image was captured. The method may further include determining a corrected measurement of the anatomical part based on the measurement correction and a measurement taken from the X-ray image.

Certain embodiments provide computer-implemented methods for calibrating an X-ray image.

Certain embodiments provide a non-transitory computer-readable medium having computer-executable instructions stored thereon, which, when executed by a processor of a computing device, cause the computing device to perform the described methods.

Certain embodiments provide a computing device comprising a memory and a processor configured to perform the described methods.

BRIEF DESCRIPTION OF THE DRAWINGS

FIGS. 27A-C illustrate example different measurements of the same anatomy portion from different X-ray images showing the need for measurement correction in accordance with various embodiments discussed herein.

DETAILED DESCRIPTION OF CERTAIN EMBODIMENTS

Figure 5:
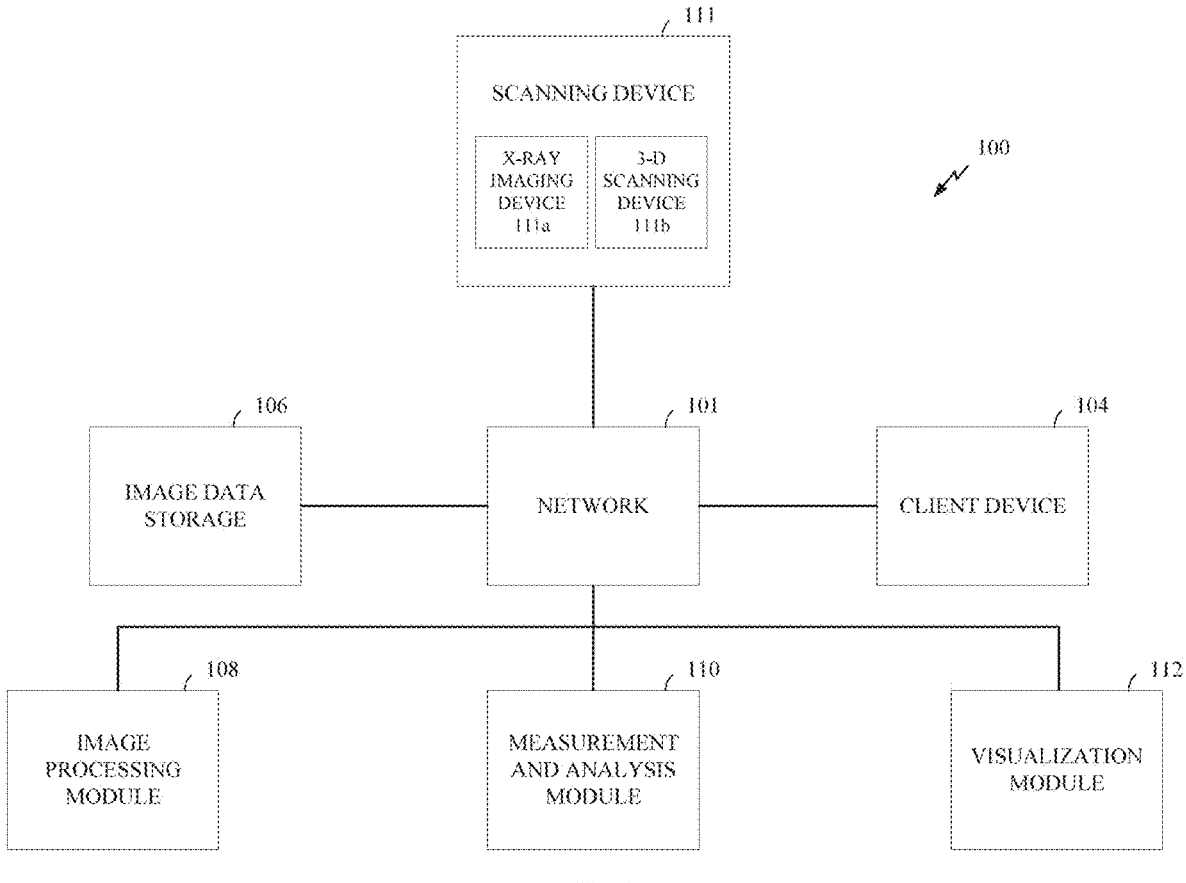
FIG. 5 is a block diagram of one example of a computing environment suitable for practicing various embodiments disclosed herein.

The systems and methods described herein may be implemented in a computing environment comprising one or more computing devices configured to provide various functionalities. FIG. 5 is an example of a computer environment 100 suitable for implementing certain embodiments described herein. The computer environment 100 may include a network 101. The network 101 may take various forms. For example, the network 101 may be a local area network installed at a surgical site. In some embodiments, the network 101 may be a wide area network such as the Internet. In other embodiments, the network 101 may be a combination of local area networks and wide area networks. Typically, the network will allow for secured communications and data to be shared between various computing devices.

Among these computing devices are a client device 104. The client device 104 may be a typical personal computer device that runs an off-the-shelf operating systems such as Windows, Mac OS, Linux, Chrome OS, or some other operating system. The client device 104 may have application software installed to allow it to interact via the network 101 with other software stored on various other modules and devices in the computing environment 100. This application software may take the form of a web browser capable of accessing a remote application service. Alternatively, the application software may be a client application installed in the operating system of the client device 104. Client device 104 may also take the form of a specialized computer, specifically designed for medical imaging work, or even more specifically for generating a computer-based representation of at least one anatomical object. The client device 104 may further take the form of a mobile device or tablet computer configured to communicate via the network 101 and further configured to run one or more software modules to allow a user to perform various methods described herein.

Figure 8:
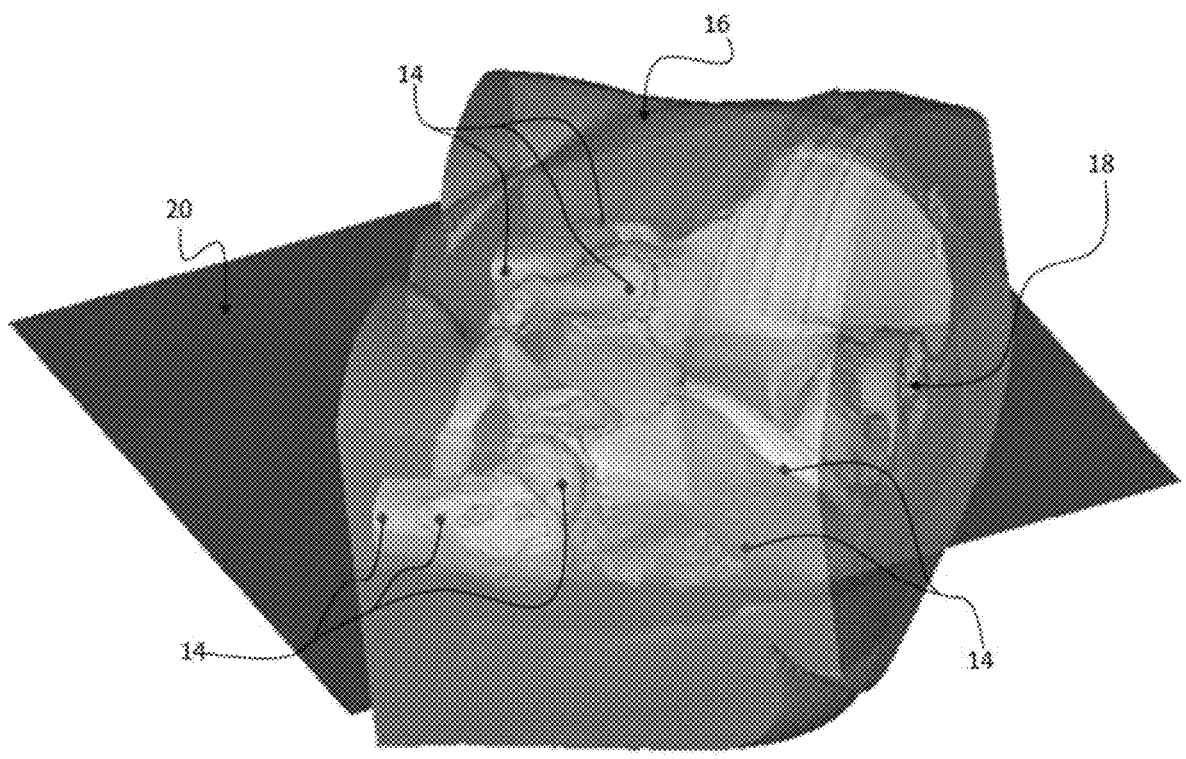
FIG. 8 depicts example anatomical landmarks on a model fitted to a 3-D surface scan image with a calibration plane in accordance with various embodiments disclosed herein.

The computer environment 100 may further include image data storage 106. Typically, the image data storage 106 takes the form of a database designed to store image files captured by a scanning device 111. According to embodiments, the scanning device 111 includes both an X-ray imaging device 111*a* and a 3-D surface scanning device 111*b*. The X-ray imaging device 111*a* includes an X-ray source 4 and a detector plate 6, and generates 2-D images 8 of skeletal (and other internal) anatomical features 10 of a subject patient 2 positioned between the X-ray source 4 and detector plate 6. The 3-D surface scanning device 111*b* may include one or more cameras, and generates 3-D surface scan images 16 of a surface of the subject patient, such as shown in FIGS. 6 and 8.

Figure 6:
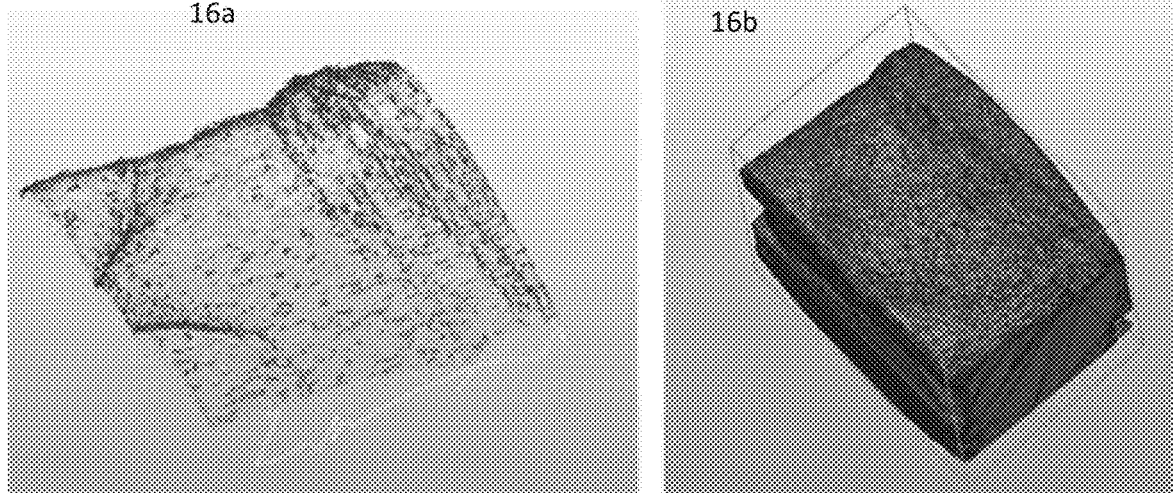
FIG. 6 illustrates example representations of a 3-D surface scan image for use in various embodiments disclosed herein.

The 3-D surface scan image 16 generated by the 3-D surface scanning device 111*b* may be visually represented as a point cloud representation 16*a* or a mesh representation 16*b*, as illustrated in FIG. 6.

The X-ray imaging device 111*a* and 3-D surface scanning device 111*b* may be positioned in in a known spatial relationship relative to each other. That is, and as will be further explained below, the 3-D surface scanning device 111*b* has a known position relative to the coordinate system of the X-ray imaging device 111*a*, and vice versa. Accordingly, the coordinates of the 2-D image generated by the X-ray imaging device 111*a* can be transformed into the coordinate system of the 3-D surface scanning device 111*b*. Likewise, the coordinates of the 3-D image generated by the 3-D surface scanning device 111*b* can be transformed into the coordinate system of the X-ray imaging device 111*a*.

The generated 2-D X-ray images 8 may be stored as Digital Imaging and Communications in Medicine (DICOM) images, or other types of image formats. The generated 3-D surface scan images 16 may be stored in any suitable format known in the art, such as DICOM, FLS, PCD, LAS, PLY, PLY2, STL and the like. The X-ray images 8 may also be added to any 3-D file having a suitable format as, for example, a pixel texture overlaid on a rectangle in an appropriate position. The image data storage 106 may be part of a scanning device 111, or alternatively it may be part of a client computing device 104. The image data storage 106 may also be in a standalone database having dedicated storage optimized for medical image data, such as a Picture Archiving and Communication System (PACS). The image data store 106 may further include in the same database or a separate database 2-D and/or 3-D digital representations/ images of implants or surgical guides, as further discussed herein. Those images may be stored in the image data storage 106.

The computing environment 100 may also include an image processing module 108. The image processing module 108 may take the form of computer software, hardware, or a combination of both which retrieves the medical imaging data from image data storage 106 and processes the 3-D surface scan images 16 and calibration data for calibrating the X-ray images 8 as further discussed herein. In some embodiments, the image processing module 108 may be provided via a web-based network application that is accessed by a computer over the network (such as client device 104, for example). Alternatively, the image processing module may be a software application that is installed directly on the client device 104, and accesses image data storage 106 via the network 101. In general, the image processing module 108 may be any combination of software and/or hardware located within the computing environment 100 which provides image processing capabilities on the image data, including 2-D X-ray images 8 and 3-D surface scan images 16 stored within the image data storage 106.

The computing environment also may include a measurement and analysis module 110 ("measurement and analysis module"). The measurement and analysis module 110 may be software that is complementary to and/or bundled with the image processing module 108. The measurement and analysis module may be an application configured to determine measurements of anatomical objects 10, such as in calibrated 2-D X-ray images of the anatomical objects 10 such as those generated according to the techniques discussed herein. As with the image processing module 108, the measurement and analysis module 110 may be a network-based application which is accessed via a web browser by one or more client devices 104. It may also be a native application installed into the operating system of a computer such as, client device 104 for example. In still other embodiments, the measurement and analysis module 110 may be a network application which is run as a client/server implementation.

The computing environment also may include a visualization module 112. The visualization module 112 may be software that is complementary to and/or bundled with the image processing module 108. The visualization module 112 may be an application configured to provide different visualizations of anatomical objects 10. For example, visualization module 112 may cause one or more 3-D models 18 and/or X-ray images 8 (e.g., after calibration or original) and/or 3-D surface scan images 16 and/or calibration planes 20 (discussed further below) to be displayed on a display of a computing device, such as client device 104, by rendering images for display. As discussed herein, the 3-D model 18 may depict an anatomical object 10 based on a statistical shape model (SSM) that is fitted to the 3-D surface scan image 16 and/or the X-ray images 8. FIG. 8 illustrates an example display generated by visualization module 112, depicting a 3-D surface scan image 16 overlaid on a 3-D model 18, with a calibration plane 20 that is determined based on anatomical landmarks 14.

Visualization module 112, as will be discussed, may render images with different colors, sizes, according to different user interfaces, etc. for display. Visualization module 112 may further render images overlaid on top of other images, such as images or renders (e.g., 2-D or 3-D) of implants on anatomical objects 10 (see FIG. 25), as further discussed herein. As with the image processing module 108, the visualization module 112 may be a network-based application which is accessed via a web browser by one or more client devices 104. It may also be a native application installed into the operating system of a computer such as, client device 104 for example. In still other embodiments, the visualization module 112 may be a network application which is run as a client/server implementation.

Figure 7:
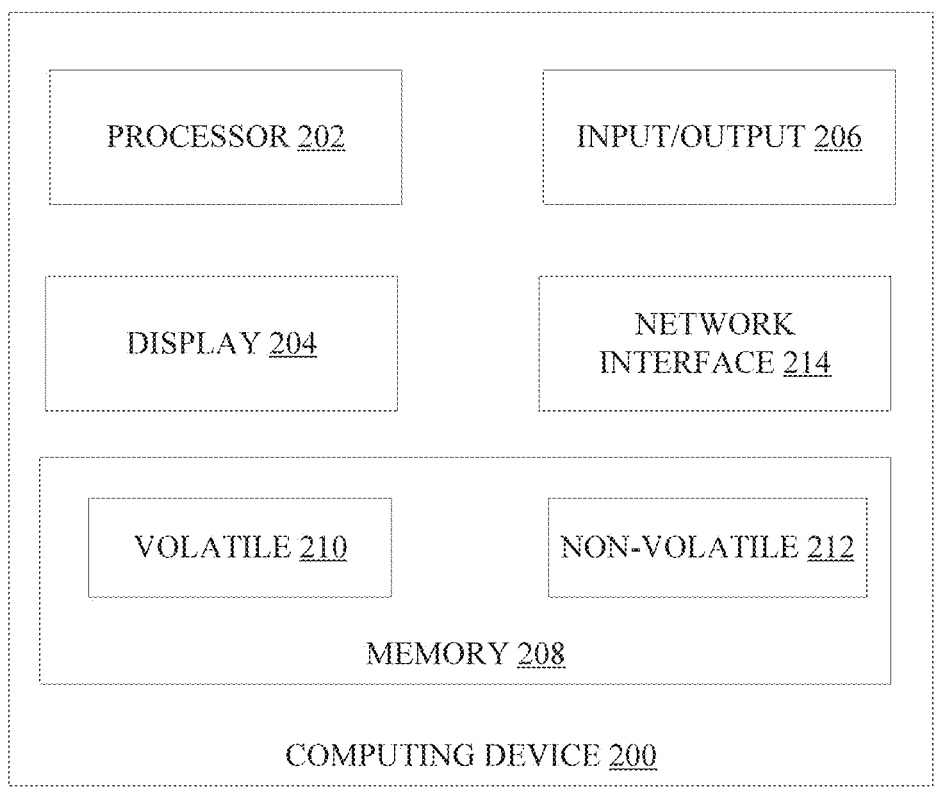
FIG. 7 is a block diagram of one example of a computing device suitable for implementing various embodiments disclosed herein.

Various embodiments of the invention may be implemented using general and/or special-purpose computing devices. Turning now to FIG. 7, an example of a computing device 200 suitable for implementing various embodiments of the invention is shown. The computer system 200 may generally take the form of computer hardware configured to execute certain processes and instructions in accordance with various aspects of one or more embodiments described herein. The computer hardware may be a single computer or it may be multiple computers configured to work together. The computing device 200 includes a processor 202. The processor 202 may be one or more standard personal computer processor such as those designed and/or distributed by Intel, Advanced Micro Devices, Apple, or ARM. The processor 202 may also be a more specialized processor designed specifically for image processing and/or analysis. The computing device 200 may also include a display 204. The display 204 may be a standard computer monitor, such as an LCD monitor as is well known. The display 204 may also take the form of a display integrated into the body of the computing device, for example as with an all-in-one computing device or a tablet computer.

The computing device 200 may also include input/output devices 206. These may include standard peripherals such as keyboards, mice, printers, and other basic I/O software and hardware. The computing device 200 may further include memory 208. The memory 208 may take various forms. For example, the memory 208 may include volatile memory 210. The volatile memory 210 may be some form of random access memory, and may be generally configured to load executable software modules into memory so that the software modules may be executed by the processor 202 in a manner well known in the art. The software modules may be stored in a nonvolatile memory 212. The non-volatile memory 212 may take the form of a hard disk drive, a flash memory, a solid state hard drive or some other form of non-volatile memory. The non-volatile memory 212 may also be used to store non-executable data, such database files and the like.

Figure 1:
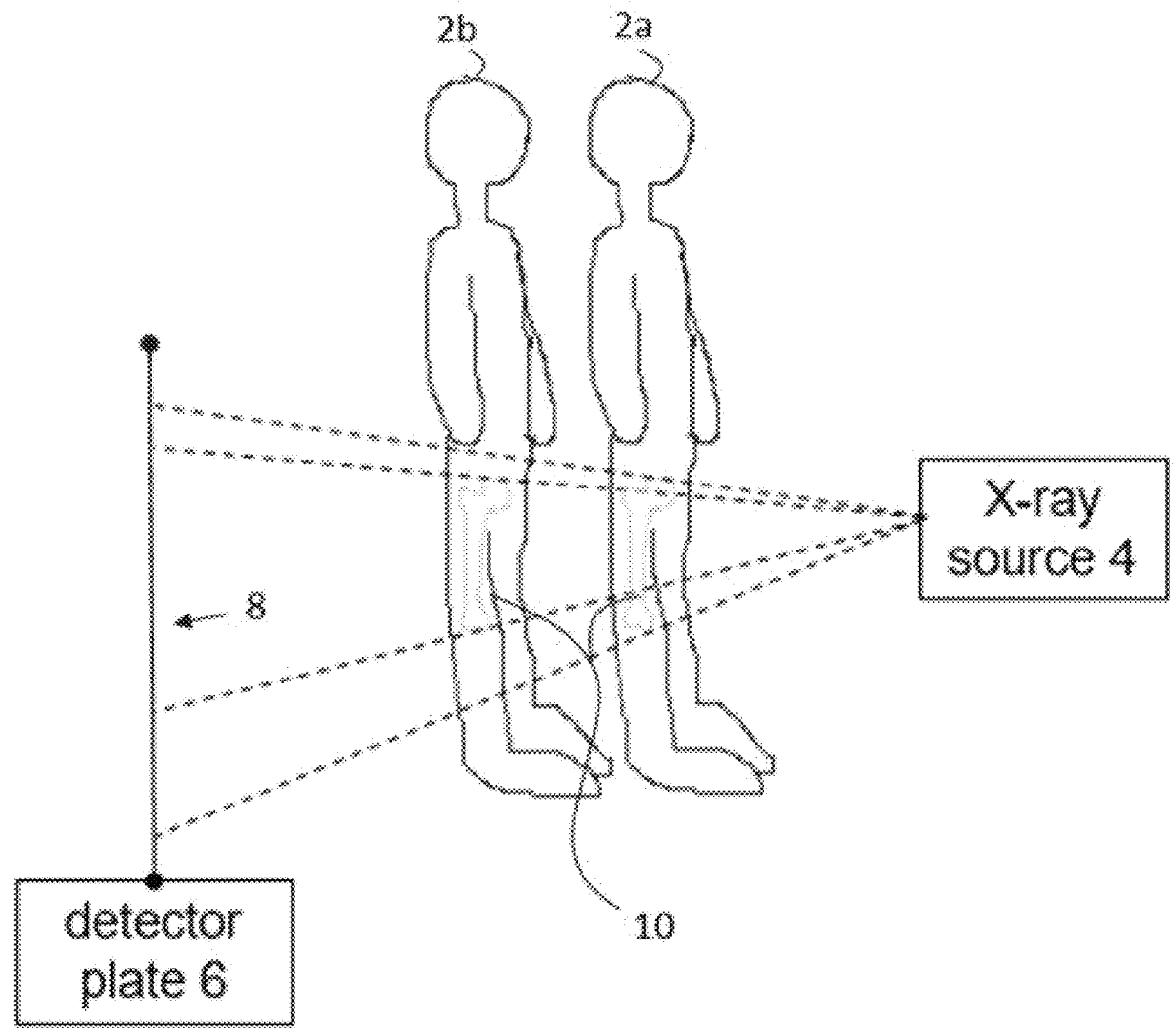
FIG. 1 illustrates an example of a subject at two different positions relative to an X-ray source and a detector plate.
Figure 2:
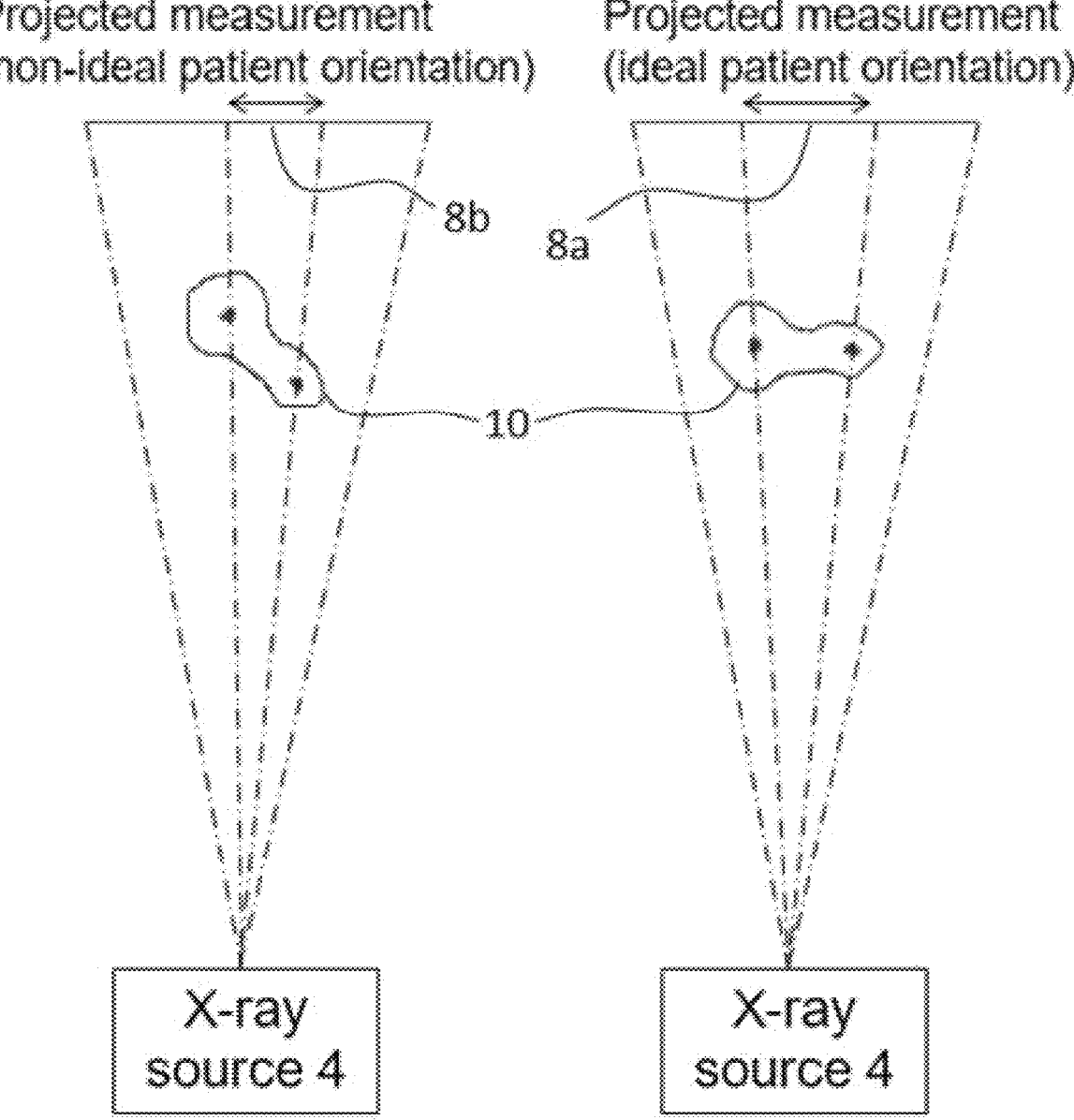
FIG. 2 illustrates an example of an anatomy portion at two different orientations relative to an X-ray source and a detector plate.

The computer device 200 also may include a network interface 214. The network interface may take the form of a network interface card and its corresponding software drivers and/or firmware configured to provide the system 200 with access to a network (such as the Internet, for example). The network interface card 214 may be configured to access various different types of networks, such as those described above in connection with FIG. 1. For example the network interface card 214 may be configured to access private networks that are not publicly accessible. The network interface card 214 may also be configured to access wireless networks such using wireless data transfer technologies such as EVDO, WiMax, or LTE network. Although a single network interface 214 is shown in FIG. 2, multiple network interface cards 214 may be present in order to access different types of networks. In addition, a single network interface card 214 may be configured to allow access to multiple different types of networks.

In general, the computing environment 200 shown in FIG. 2 may generally include one, a few, or many different types of computing devices 200 which work together to carry out various embodiments described below. A skilled artisan will readily appreciate that various different types of computing devices and network configurations may be implemented to carry out the inventive systems and methods disclosed herein to provide the system 200 with access to a network (such as the Internet, for example). The network interface card 214 may be configured to access various different types of networks, such as those described above in connection with FIG. 1. For example the network interface card 214 may be configured to access private networks that are not publicly accessible. The network interface card 214 may also be configured to access wireless networks such using wireless data transfer technologies such as EVDO, WiMax, or LTE network. Although a single network interface 214 is shown in FIG. 2, multiple network interface cards 214 may be present in order to access different types of networks. In addition, a single network interface card 214 may be configured to allow access to multiple different types of networks.

In general, the computing environment 200 shown in FIG. 2 may generally include one, a few, or many different types of computing devices 200 which work together to carry out various embodiments described below. A skilled artisan will readily appreciate that various different types of computing devices and network configurations may be implemented to carry out the inventive systems and methods disclosed herein.

3-D Scan to Features for Calibration

In certain embodiments, a 3-D surface scan image 16 generated by the 3-D scanning device 111b is represented as a point cloud representation 16a, a mesh representation 16b (see FIG. 6) or a patient avatar expressed in the coordinate system of the image source (e.g., the camera(s) of the 3-D scanning device 111b) or any coordinate system that can be related to this coordinate system. The 3-D coordinates of every point or every object in the point cloud representation 16a or mesh representation 16b are expressed in a local coordinate system attached to the image source. Every X-ray image 8 generated by the X-ray imaging device 111a comes with a corresponding 3-D surface scan image 16, taken simultaneously, or at least with the patient 2 in a fixed position. For each such pair of 3-D surface scan image 16 and X-ray image 8, the spatial relationship between the coordinate system of the 3-D scanning device 111b and the coordinate system of the X-ray imaging device 111a is known, such as based on the known position and orientation of the X-ray imaging device 111a and the 3-D scanning device 111b with respect to one another. This allows relating the coordinates of the objects in the 3-D surface scan image 16 to the coordinate system of the X-ray imaging device 111a, and therefore determining the relative position (e.g., location and orientation) of the actual surface that was scanned with respect to the X-ray source 4 and detector plate 6 of the X-ray imaging device 111a. As discussed herein, it is understood that the position of a 3-D object in space (e.g., in a coordinate system) is defined by 6 degrees of freedom: 3 relating to location and 3 relating to orientation.

The 3-D surface scan image 16 (e.g., the underlying data) can be expressed in the coordinate system of the X-ray imaging device 111a. Alternatively, 3-D surface scan image 16 can be expressed in another coordinate system, such as a local coordinate system of the 3-D scanning device 111b, as long as the appropriate transformation from that local coordinate system to the coordinate system of the X-ray imaging device 111a is known.

In certain embodiments, the 3-D surface scan image 16 is used as a representation of the patient skin surface. When used intra-operatively, the 3-D surface scan image 8 may also capture anatomical information underneath the skin such as bone surfaces or implant components, e.g., anatomy 10 or hardware that normally lies beneath the skin, but becomes visible in the surgical window (is exposed by the surgeon).

Figure 3:
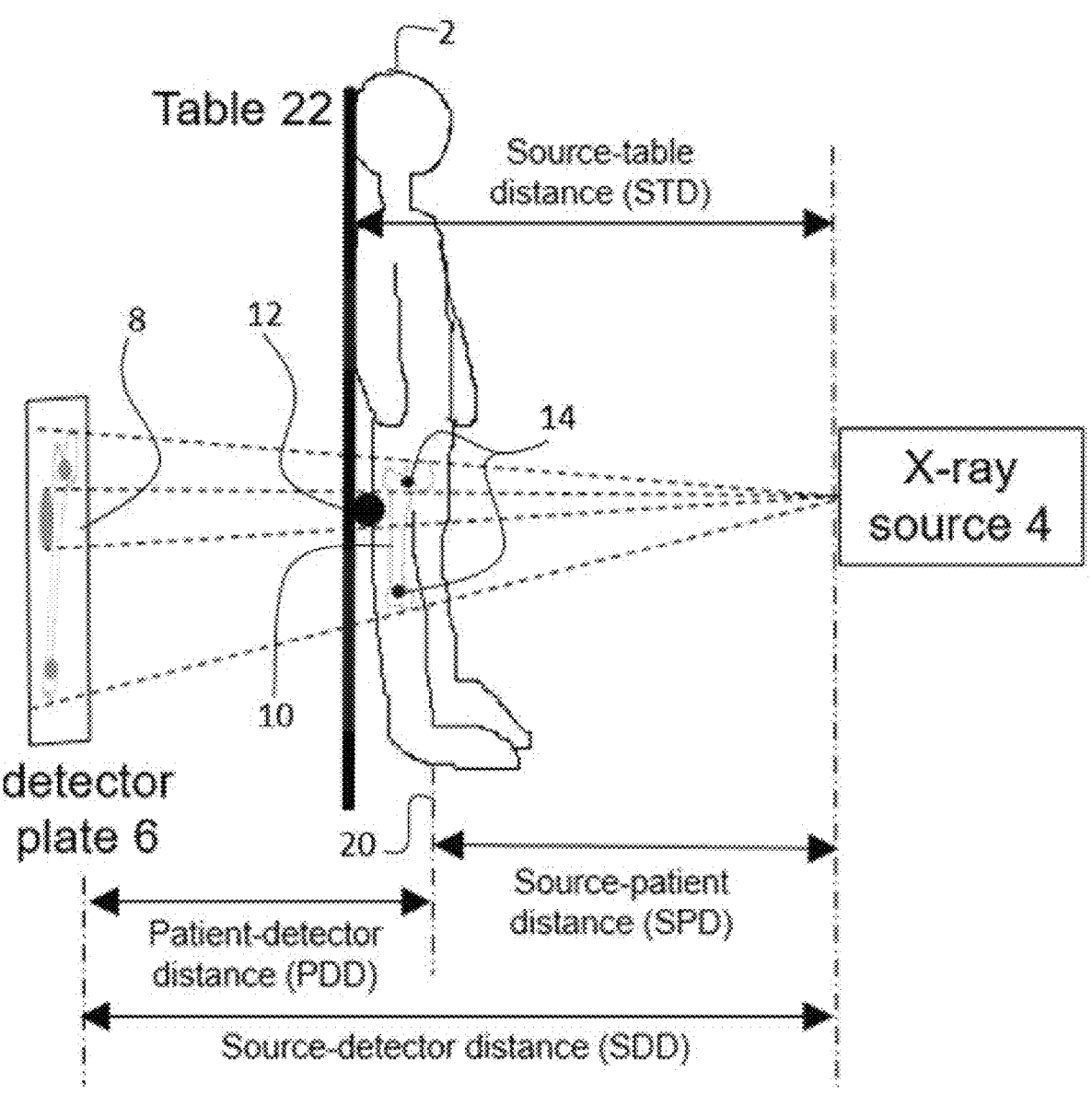
FIG. 3 illustrates an example of a subject and a calibration marker positioned between an X-ray source and a detector plate.
Figures 4A, 4B, 4C, 4D:
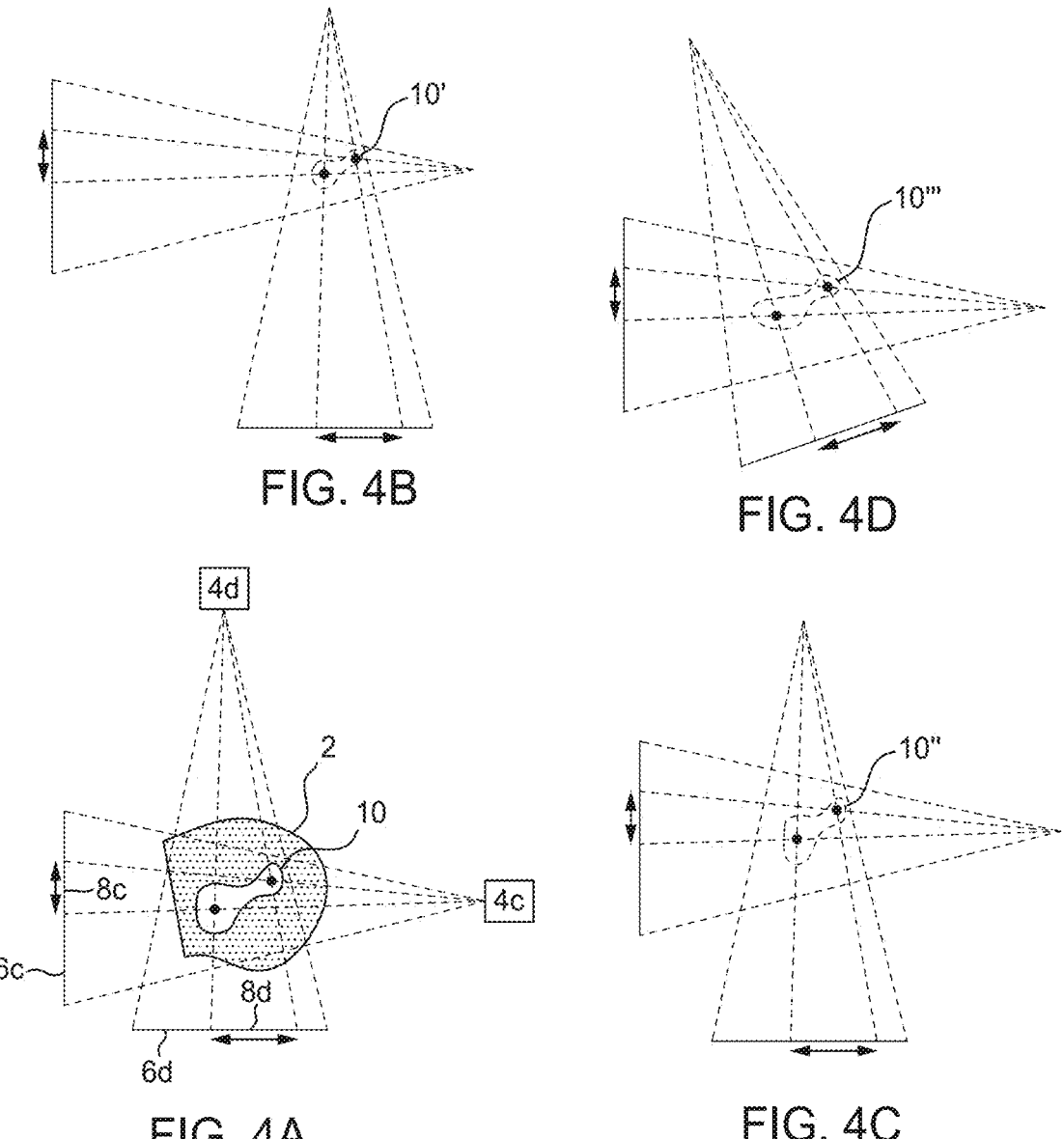
FIG. 4A-D illustrate an example of size and proportions of an anatomy portion depicted in an X-ray image depending on position and orientation of the anatomy portion relative to an X-ray source and a detector plate.
Figure 4E:
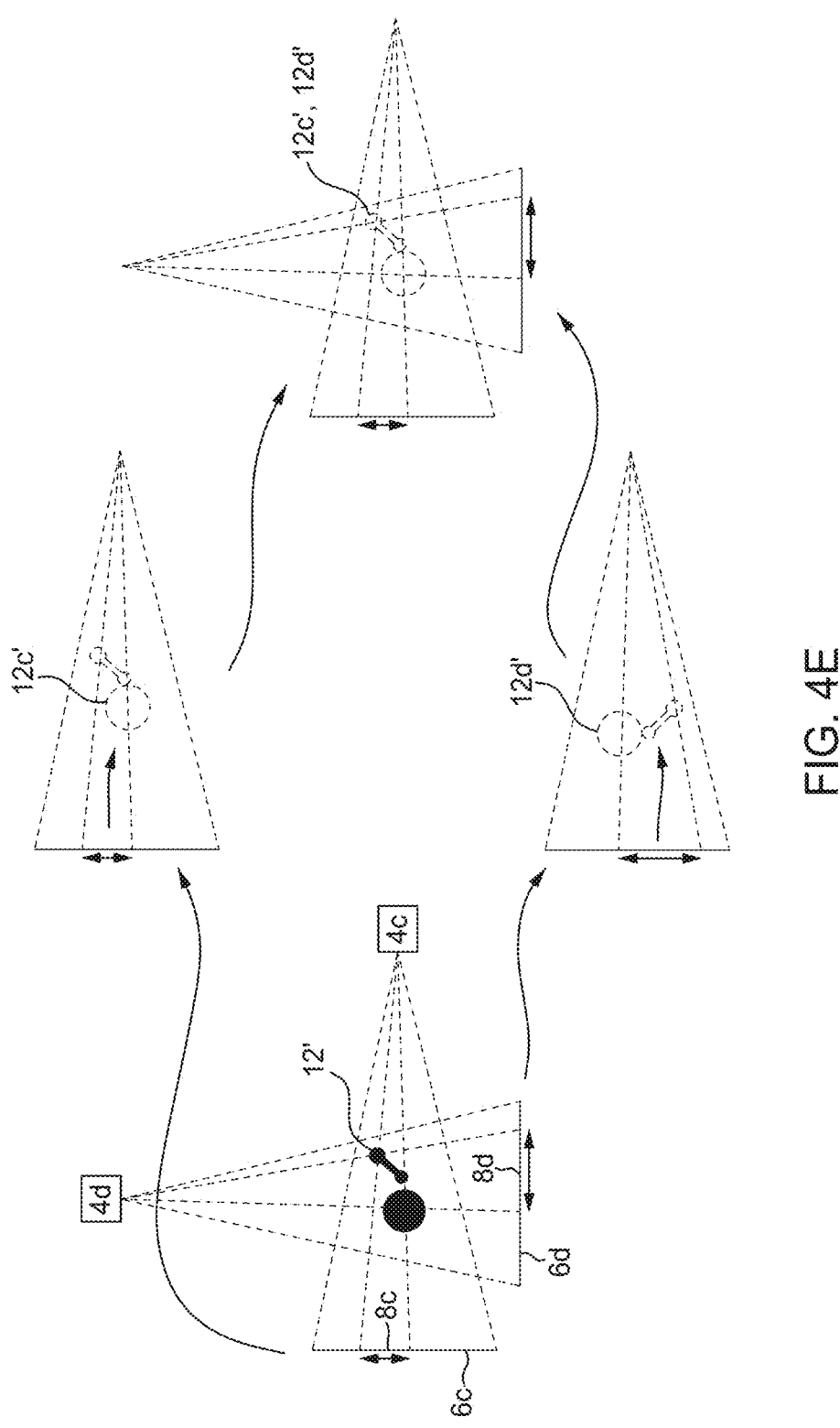
FIG. 4E depicts an example of an elaborate calibration marker for registering multiple X-ray images.

In certain embodiments, the 3-D surface scan image 16 may be separated into a model of the patient 10 (e.g., 3-D body model or patient avatar model) and a model of a table 22 on which the patient 2 is positioned, e.g., to determine the dimensions of the patient 10 by obtaining one or more of the patient-to-detector distance (PDD), source-to-patient distance (SPD) and the source-to-table (STD) distance separately. FIG. 3 depicts a simple formula that represents one example whereby a dimension of the patient 2 is based on a plane through the patient 2 at which the SPD is calculated.

The plane through the patient 2 at which the SPD is calculated—calibration plane 20—may be based on the body outline, e.g. through an anterior point of the body outline, or halfway through the patient 2 or any other plane. As will be described in more detail below, the use of such a calibration plane 20 based on 3-D surface scan image 16 allows for more accurate scaling of X-ray image 8 or performing more accurate measurements based on X-ray image 8 without the need for a calibration marker.

In certain embodiments, the 3-D surface scan image 16 may be used to determine the position of multiple X-ray sources 4 in relation to the anatomy 10 of the patient 2, e.g., when the patient 2 has moved between multiple acquisitions of X-ray images 8. As described above, each X-ray image 8 comes with a 3-D surface scan image 16 of the imaged patient 2 in the same or very nearly the same position with respect to the X-ray imaging device 111*a* that the patient was in at the time the corresponding X-ray image 8 was generated. That is, the X-ray image 8 and its corresponding 3-D surface scan image 16 are generated more or less simultaneously and/or without the patient changing positions.

Each of the resulting 3-D surface scan images 16 is expressed in a coordinate system attached to the scanning device 111 corresponding to the subject's position at the time of imaging, or in another coordinate system that allows finding the correct spatial relationship between the 3-D surface scan image 16, the X-ray source 4 and the detector plate 6, and therefore the X-ray image 8. The different 3-D surface scan images 16 can be registered on top of one another (e.g. using iterative closest point technique) and the X-ray sources 4, detector plates 6 and X-ray images 9 can be likewise registered by applying the same rigid transformation. The result is that the multiple X-ray images 8 are brought into a common coordinate system, e.g. they are registered. As will be described in more detail below, registering multiple X-ray images 8 based on their corresponding 3-D surface scan images 16 allows, for example, reconstructing 3-D models based on multiple X-ray images without the need for an elaborate calibration marker.

In certain embodiments, the 3-D surface scan image 16 may be used to determine anatomical landmarks 14 (bony and/or soft-tissue), geometric features derived from anatomical landmarks 14 (e.g., anatomical planes, midplanes, occlusal planes, anatomical axes, mechanical axes, midlines, anatomical coordinate systems, and the like), or measurements derived from anatomical landmarks 14 (e.g., distances, widths, lengths, etc.) on the patient 2. FIG. 8 depicts example anatomical landmarks 14 on a model fitted to a 3-D surface scan image 16.

In some embodiments, anatomical landmarks may be identified directly on the 3-D surface scan image 16. For example, for hip or knee surgery, the landmarks 14 could comprise the iliac crest, the knee, the epicondyles of the femur, the patella, the ankle, the medial malleolus, the lateral malleolus. As another example of anatomical landmarks 14, for craniomaxillofacial (CMF) surgery, the landmarks 14 could comprise any facial features, such as the nose, the tip of the nose, nostrils, the trichion, the nasion, the tragus, the cheilion, the gonion, the pogonion, the endocanthion, the ectocanthion. As an example of a feature that can be determined from anatomical landmarks 14, the central axis of the tibia can be determined from the epicondyles and the malleoli as the line connecting the midpoint between the epicondyles and the midpoint between the malleoli. As an example of a measurement that can be determined from anatomical landmarks 14, width of the distal femur may be determined as the distance between the epicondyles.

Anatomical landmarks 14 may be identified manually by an operator or automatically. For example, in certain embodiments, determining one or more anatomical landmarks 14 may be done using machine-learning or more traditional feature-recognition or measurement algorithms on the 3-D body model or surface scan. An overview of current machine-learning techniques applicable to certain embodiments described herein can be found in: Griffiths, D., Boehm, J., A Review on Deep Learning Techniques for 3D Sensed Data Classification, in: Remote Sens. 2019, 11, 1499. Traditional feature-recognition algorithms applicable to certain embodiments described herein may include rule-based techniques, such as curvature analysis to find a ridge or an apex. Traditional measurement algorithms applicable to certain embodiments described herein may include measurements manually identified by an operator.

In certain embodiments, measurements on the 3-D surface scan image 16 may be used to calibrate or correct measurements on the corresponding X-ray image 8. For example, a measurement on the 3-D surface scan image 16 can be determined, which corresponds to a measurement on the associated X-ray image 8, thereby determining the scaling factor between the two. For example, a knee's epicondyles can be identified on both a 3-D surface scan image 16 and a frontal X-ray image 8 of the knee. The distance between both epicondyles may be measured on both the 3-D surface image scan 16 and the X-ray image 8. The ratio between the two provides a scaling factor to correct other measurements taken from the X-ray image 8. If the measurement taken from the X-ray image 8 is based on the depiction of bony anatomy, a correction of one of the distances may be necessary to account for the presence of soft tissue. If the measurement taken from the X-ray image 8 is based on the depiction of soft tissue (e.g. measuring from skin to skin), such a correction may not be necessary.

More complex examples can be implemented, where comparisons of measurements in roughly perpendicular directions (e.g. between the epicondyles versus along the longitudinal axis of the tibia, as discussed above) can produce differing scale factors that can be used to perform more accurate scaling corrections (e.g. in the case of a moving X-ray source 4, the first could be used for horizontal measurements and the second for vertical measurements), or to account for the patient 2 or the anatomy 10 10 of interest not being correctly aligned with the X-ray imaging device 111*a*. For example, as illustrated in FIGS. 27A-C, to correct measurements taken from a non-frontal X-ray image 8 of a leg where a frontal X-ray image 8 is expected/needed, separate scaling factors may be determined for horizontal measurements (accounting for both the perspective projection and the foreshortening due to a possible internal or external rotation of the leg) and vertical measurements (accounting for both the perspective projection and the foreshortening due to a possible flexion of the leg). FIG. 27A shows a frontal X-ray image 8 of a hip joint of a patient with femur 10 in neutral position. Two measurements 272a, 272b are taken from the X-ray image 8: measurement 272a is the horizontal distance between the center of the femoral head and the anatomical axis of the femur, also referred to as the femoral offset; measurement 272b is the vertical distance between the center of the femoral head and the top of the lesser trochanter, also referred to as the vertical offset. FIG. 27B shows an X-ray image 8 of the same hip joint in which the leg is externally rotated and slightly flexed. FIG. 272C shows an X-ray image 8 of the same hip joint in which the leg is internally rotated and slightly extended. The internal/external rotation and flexion/extension may lead to incorrect horizontal and vertical measurements, respectively. Separate scaling factors may therefore be determined to correct horizontal and vertical measurements. Slanted measurements may be decomposed into perpendicular components, and the appropriate scaling factors may be applied to both components.

Figure 9:
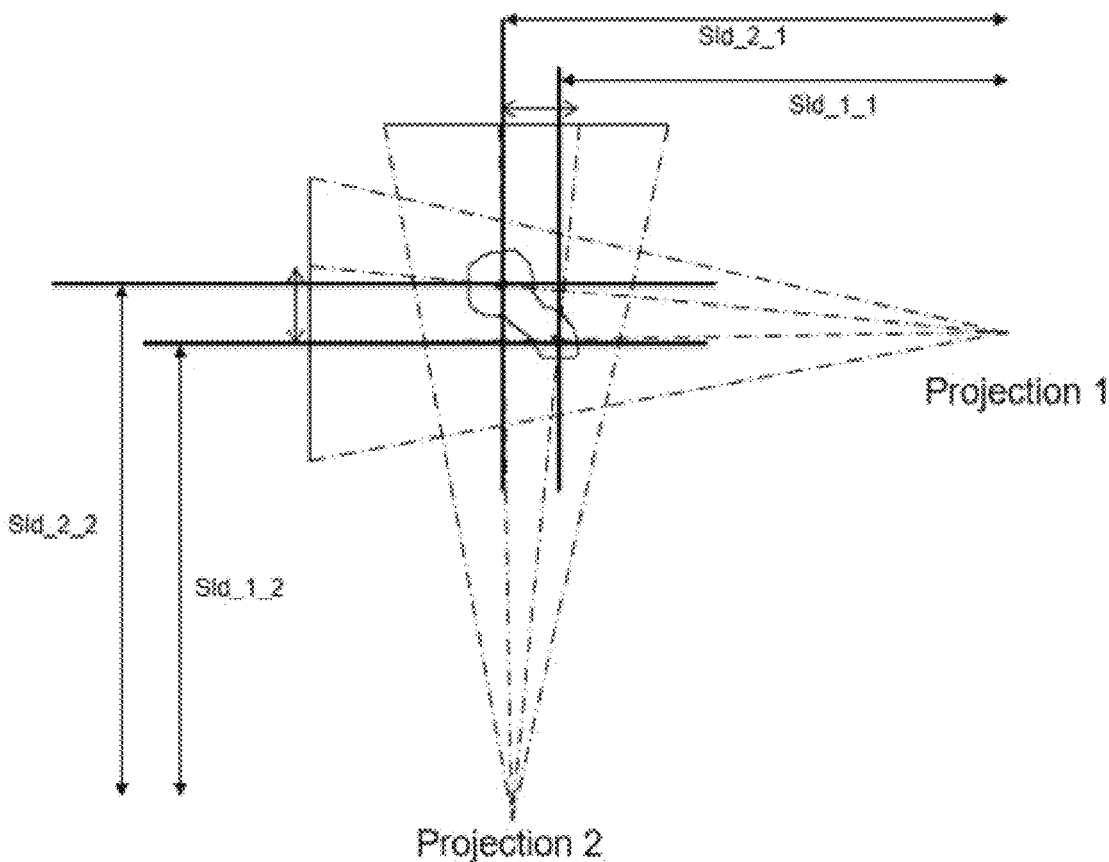
FIG. 9 depicts an example of determining a 3-D position of an anatomy portion from multiple X-rays in accordance with various embodiments disclosed herein.

Alternatively, as illustrated in FIG. 9, after registration of multiple X-ray images, it is possible to assess 3-D positions of landmarks by back-projecting them: The 3-D position of a particular landmark can be found as the intersection of the projection rays from the X-ray sources 4 to the depictions of a particular landmark in mutually registered X-ray images 8. Measurements can then be taken based on these 3-D positions, rather than from the X-ray images, and hence distances can be calculated between landmarks which are not affected by patient orientation.

Measurement comparisons to determine scaling factors may also be done in collaboration with a statistical shape model (SSM) to determine the position of internal anatomies 10 and anatomical landmarks 14 of the patient 2, or external anatomies or anatomical landmarks 14 present on a surface of the patient that is not part of the 3-D surface scan image 16 (e.g. the back of a patient scanned in supine position). As an example, an SSM of external patient anatomy may be constructed from a training set of 3-D surface scan images of a large population. Optionally, the locations of external anatomical landmarks 14 may be identified in the training set and included in the SSM. Alternatively or additionally, an SSM may be constructed of both external and internal anatomy and/or anatomical landmarks. For example, from a set of CT or MRI data sets, the outer skin surface can be segmented. Additionally, certain internal anatomical parts 10 can be segmented and/or certain internal and/or external anatomical landmarks 14 can be identified. If the resulting 3-D model(s) and any identified anatomical landmarks 14 (e.g. as metadata) are grouped into a single 3-D model for each specimen, a training set can be created. From the training set, an SSM can be created. Various techniques for creating SSMs are known in the art (e.g. U.S. Pat. No. 9,977,993). The SSM will encode in a parameter vector the correlations between shape variations and, if available, locations of anatomical landmarks 14 among all the specimens of the training set.

The SSM may then be fit onto the 3-D surface image scan 16 or an isolated part of 3-D surface image scan 16 by determining the values for the parameter vector that provide the best match between the 3-D surface scan image 16 and the 3-D model of the skin surface of the SSM. Any shapes of internal or external structures or locations of identified anatomical landmarks 14 available in the SSM will follow the deformation of the skin surface according to the shape correlations encoded into the SSM. The resulting SSM instance can be used to approximate the shapes and/or locations of any internal or external structures or landmarks that can otherwise not be directly derived from the 3-D surface scan image 16.

Using this technique, many more anatomical landmarks 14 (e.g. internal anatomical landmarks 14, such as the center of the femur head, or landmarks on surfaces facing away from the 3-D scanning device 111b) become available, for example for determining a calibration plane 20 or for measurement comparison between the 3-D model and the X-ray image 8 (e.g. to perform scaling corrections).

As an example, an SSM that includes the body contour of a particular region of the patient 2 as well as internal anatomy 10 may be fit to the 3-D surface scan image 16 or a body model, resulting in an SSM instance. From this SSM instance, a 3-D model of the bony anatomy 10 can be derived and/or the resulting anatomical landmarks 14 can be identified. The anatomical landmarks 14 may already be part of the SSM, and they will be moved to the right location when the SSM is fitted to the 3-D surface image scan 16. Alternatively, 3-D models of internal anatomical parts 14 (e.g. bones or organs) may be present in the SSM and their shapes will be deformed along with the 3-D model of the skin when the SSM is fitted to the 3-D surface scan image 16. In that case, the anatomical landmarks 14 can be identified manually or automatically on the resulting 3-D models of the internal anatomy 10.

Either way, fitting the SSM can deliver information on the locations of internal or external anatomy 10 or anatomical landmarks 14 that can normally not be identified on a 3-D surface scan image 16 of the patient.

For example, a 3-D surface scan image 16 representing the skin combined with 3-D models of one or more underlying bones, 3-D locations of one or more anatomical landmarks on and/or in the underlying bones can be identified. These may be used to determine a calibration plane 20 or for performing measurement comparisons as described herein, e.g. to perform measurement corrections.

In certain embodiments, the 3-D surface scan image 16 may be used to understand and determine the pose of the patient 2 as a whole or the pose of individual limbs or joints, e.g., patient limb orientation in relation to the plane of the X-ray detector plate 6 and X-ray source 4 and, using this, give feedback on the accuracy with which the clinical positioning protocol (e.g., the imaging protocol) was implemented by the patient and radiologist. For example, it may be identified from the 3-D surface scan image 16, or from anatomical landmarks 14 identified on the 3-D surface scan image 16, that a patient's leg was internally or externally rotated over x degrees with respect to the X-ray detector plate 6 and X-ray source 4 at the time of acquisition of the X-ray image 8. This information may be used to advise the clinician who uses the X-ray image 8 for planning a hip replacement that a femoral neck length measurement taken from the X-ray image 8 may not be accurate, so as to avoid the implantation of a hip implant with an inappropriate femoral offset.

However, going one step further, the information may be used to correct the femoral neck length measurement taken from the X-ray image 8 to account for the x degrees of internal or external rotation, for example, by applying not only a scaling factor to account for the perspective projection, but also a correction factor of $1/\cos(x)$ to any measurements substantially perpendicular to the axis of internal/external rotation (e.g. to horizontal measurements).

In certain embodiments, the determining of patient limb orientation may also be done in combination with machine learning or the use of statistical models as described above to determine the position of the internal landmarks. Machine learning may be used to learn the correspondence between features visible on the 3-D surface scan image 16 and anatomical landmarks 14 on the soft-tissue or bony anatomy 10 of the patient 2. Machine learning performs a similar function here as the function of the SSM described herein. For example, a dataset may be compiled whereby medical images such as CT images are acquired from a series of patients. From these CT images, anatomical models are constructed of the body contour (simulating the 3-D surface scan image 16) and the internal anatomy 10 such as the bony anatomy. On these anatomical models, anatomical landmarks 14 on the body contour and the internal anatomy 10 are annotated. Machine-learning techniques are used to learn the relationship between the anatomical landmarks 14 on the body contour and the internal anatomical landmarks 14. From a 3-D surface scan image 16, the anatomical landmarks 14 on the body contour can be (automatically) annotated. Based on these, the machine-learning model can be applied to predict the internal landmarks 14.

The pose of the patient 2 as a whole or the pose of individual limbs or joints may also be determined based on the 3-D surface scan image 16, for example through traditional pose estimation techniques based on anatomical landmarks 14, optionally coupled to an SSM of patients or specific body parts, limbs or joints. For example, an average head model in the natural head position may be used as a reference. Anatomical landmarks 14 detected on the 3-D surface scan image 16 in combination with (corresponding) landmarks 14 in the head model may be input into a pose estimation algorithm. An overview of pose estimation approaches may be found in "Deep 3-D human pose estimation: A review", by Wang. Et al, Computer Vision and Image Understanding, Volume 210, September 2021.

In certain embodiments, anatomical landmarks 14 or measurements of bony structures from the X-ray image 8 may be used to support the machine learning or SSMs, e.g., by determining relative distances between anatomical landmarks 14 on the X-ray images 8 or by extracting body contours or bony anatomy contours. First, anatomical landmarks 14 are detected on the X-ray images 8 using any suitable manual or automatic landmark detection techniques. Then, these anatomical landmarks 14 may be converted into measurements, e.g. distances between anatomical landmarks 14. The machine-learning model that describes the relationship between anatomical landmarks visible on the 3-D surface scan image 16 and internal anatomical landmarks 14 may be complemented with these measurements. For example, these measurements could have been extracted from the CT data and added to the data during the construction of the machine-learning model. The relative measurements on the X-ray image 8 were unavailable in the 3-D surface scan image 16, and including them can thus increase its predictive value.

As an example: the hip centers for both left and right hip may be detected in the X-ray image 8. Also, the body contour may be detected on the X-ray image 8. The ratios between the distance between the hip centers and the width of the body in the coronal or sagittal plane may be determined. These ratios may be added to the machine learning model to predict the location of the hip center landmarks based on the 3-D surface scan image 16.

In certain embodiments, the anatomical landmarks 14 or derived data points that may be determined include one or more of:

For hip: one or more of femoral neck axis, center of femoral head, greater trochanter, innominate tuberosity of the femur, the anterior superior iliac spine, pubic joint, femoral neck axis, etc.;

For knee: one or more of center of the patella, midway point between anterior and posterior surface of the tibia, anterior and posterior surfaces of the distal femur, midway point between anterior and posterior surface of the femur, facies patellaris saddle point, center point of lateral tibial plateau, center point of medial tibial plateau, medial intercondylar tubercle of the tibia, lateral intercondylar tubercle of the tibia, tibial tuberosity, anterior intercondylar area of the tibia, width of the knee excluding soft-tissue, etc.;

For ankle: one or more of medial or lateral malleolus, etc.;

For the foot: one or more of metatarsal, etc.; and

For the shoulder: one or more of acromion process, coracoid process, glenoid, center of the glenoid, most medial point of the scapula, most medial point of scapular spine, humeral head, center of humeral head, etc.

In certain embodiments, the patient-to-detector distance (PDD) or source-to-patient distance (SPD) may be determined based on a calibration plane 20 fitted to any combination of internal anatomical landmarks 14 or anatomical landmarks 14 on the 3-D surface scan image 16. For example, the PDD or SPD may be determined by fitting a plane parallel to the plane of the detector plate 6 through the most proximal or distal point on the 3-D surface scan image 16. In another example, the PDD or SPD may be determined based on anatomical landmarks 14 inside the patient 2 (e.g., the neck-shaft plane or the most lateral point of the greater trochanter for hip arthroplasty).

Figure 10:
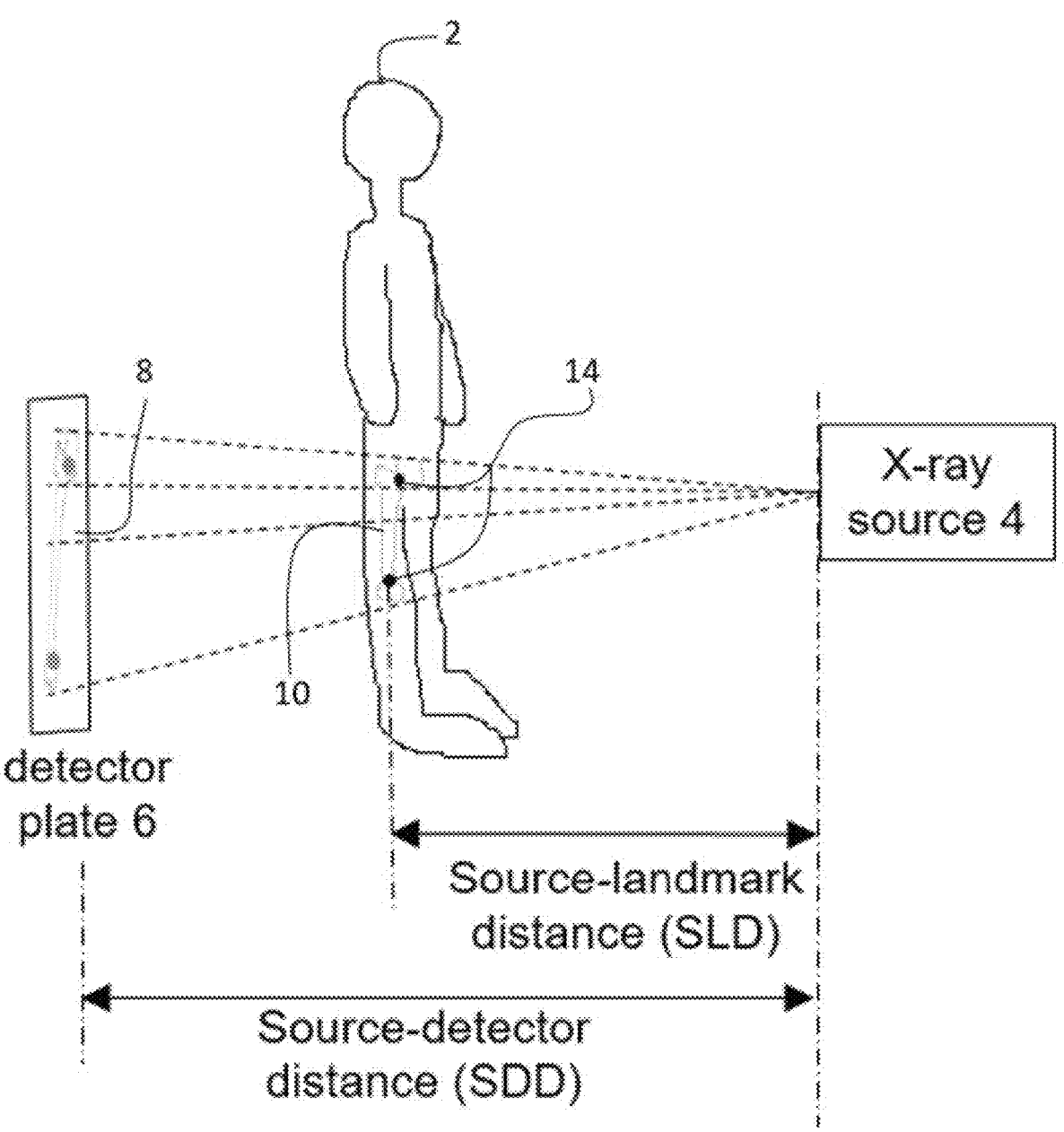
FIG. 10 illustrates an example of a subject positioned between an X-ray source and a detector plate and anatomical landmarks of the subject being used to determine a scaling factor for correcting measurements from an X-ray image in accordance with various embodiments disclosed herein.

As described above and as illustrated in FIG. 10 (see also FIG. 3), the location of the imaged subject (e.g. patient 2 or anatomy 10 of interest) between the X-ray source 4 and the detector plate 6 determines the correct scaling factor needed to obtain accurate measurements from an X-ray image 8. Assuming, for example, a point X-ray source 4, the X-ray image 8 of a feature with a dimension m, measured parallel to the detector plate 6, will be a projection with a corresponding dimension m*SDD/SPD, in which SDD is the distance from the X-ray source 4 to the detector plate 6 and SPD is the distance from the X-ray source 4 to the subject. Both distances are measured perpendicular to the detector plate 6. Knowing these distances therefore allows determining an appropriate scale factor to measurements taken from the resulting X-ray image 8. For example, a measurement m1 of the diameter of a femoral head taken from the X-ray image 8 will correspond to an actual femoral head diameter of m1*SPD/SDD.

In these formulae, SPD can be substituted with (SDD–PDD) in which PDD is the patient-to-detector distance, again measured perpendicular to the detector plate 6.

Knowing PDD or SPD, and SDD therefore allows correct scaling without the need for using a calibration marker 12.

Having the 3-D surface scan image 16 in the same coordinate system as the X-ray image 8 (or at least being able to bring the two in the same coordinate system) allows for determination of an appropriate PDD or SPD for the desired measurement. For example, for a series of measurements on or surrounding the patient's knee, the center of gravity of a part of the 3-D surface scan image 16 representing the knee can be determined. The perpendicular distance from this point to the detector plate 6 can be used as PDD in the formulae above. This is the same as the distance between the detector plate 6 and a plane parallel to the detector plate 6 through the center of gravity.

Depending on the required accuracy, instead of the center of gravity, a plane parallel to the detector plate 6 and through the popliteal or through the most anterior point of the patella may also give acceptable results.

If particular internal anatomical structures or distances between particular internal anatomical landmarks 14 are to be measured, the locations of these internal structures or anatomical landmarks 14 may be determined by means of the methods described above (e.g. by fitting an SSM comprising surface data representing the skin and geometrical information about these structures or anatomical landmarks 14 onto the 3-D surface scan image 16). These locations may be used to determine an appropriate SPD or PDD, for example, by calculating the center of gravity of an internal structure and subsequently the distance from this center of gravity to the detector plate 6, by calculating the average distance from the set of anatomical landmarks 14 of interest to the detector plate 6, or by fitting a plane parallel to the detector plate through one or more anatomical structures or anatomical landmarks 14.

Example Calibration Methods Based on Features from 3-D Surface Scan

In certain embodiments, algorithms are provided to find a corresponding measurement between the same anatomical landmarks 14 in the 3-D surface scan image 16 and in the X-ray image 8 thereby determining a scaling factor between the two datasets. For example, the algorithm may be based on soft-tissue alone or on internal (e.g., bony) anatomy or a combination.

In certain embodiments, the source-patient distance (SPD) and source-detector distance (SDD) may be used to perform the scaling factor calculation, in combination with the imager resolution. Alternatively, the patient-detector distance (PDD) and the SDD may be used. In the following, formulae will be based on SPD rather than PDD, but equivalent formulae can be easily found by replacing SPD with SDD−PDD. The source-patient distance (SPD) may be chosen based on the 3-D surface scan image 16 itself (e.g., choosing a point on the outer body contour of the patient 2 or fitting a calibration plane 20 to parts of the outer body contour of the patient 2) or may be calculated in combination with a population model to choose a calibration plane 20 corresponding to anatomical landmarks 14 inside the patient (e.g., a plane parallel to the plane of the detector plate 6 through the center of the femoral head, or the plane through the center of the femoral head, the femoral neck and the femoral shaft for hip arthroplasty).

"Population model" here may refer to an SSM that combines a 3-D surface model of the skin with 3-D data of internal structures and/or anatomical landmarks (e.g. 3-D surface model of an anatomical part 10 or 3-D coordinates of a certain anatomical landmark 14).

Fitting a calibration plane 20 as discussed herein refers to choosing an appropriate SPD (or PDD): picking a plane that passes through the landmark of interest, the anatomical structure of interest, or, if there are more than one landmark or structure of interest, as close as possible to all of them. The plane may or may not be chosen to be parallel to the detector plate 6. If it is parallel to the detector plate 6, a single SPD may be determined as the perpendicular distance from the source to the calibration plane 20. Alternatively, a single PDD may be determined as the distance between the calibration plane 20 and the plane of the detector plate 6.

Examples of a suitable plane parallel to the detector plate 6 include:

through the center of the femoral head;
through the midpoint of the femoral neck axis;
through the greater trochanter;
center of the femoral head/neck/shaft plane; and
center of gravity of the triangle formed by the center of the femoral head, the greater trochanter and the facies patellaris saddle point The single SPD value may then be used to calculate a correction scaling factor equal to SPD/SDD for all measurements taken on the X-ray image 8. For example, if the X-ray image 8 has an image resolution R (the ratio between a distance measured in the X-ray image, often expressed in pixels, and the corresponding real-world distance measured in the plane of the detector plate 6, often expressed in inch or mm), a measurement $\Delta L_{image}$ taken on the X-ray image 8 can be corrected to a corresponding measurement $\Delta L_{patient}$ on the anatomy of the patient 2 according to the formula:

$$\Delta L_{patient} = \Delta L_{image} \cdot \frac{1}{R} \cdot \frac{SPD}{SDD}$$

For the sake of efficiency and clarity, the scaling with 1/R to account for image resolution will be considered in the remainder of this disclosure to be automatically incorporated into the image-based measurement, yielding an adjusted formula:

$$\Delta L_{patient} = \Delta L_{image} \cdot \frac{SPD}{SDD}$$

The scaling factor SPD/SDD will, in this case, only be correct for X-ray image-based measurements that correspond to real-world measurements within calibration plane 20. It will be too small for all real-world measurements that lie between the calibration plane 20 and the plane of the detector plate 6 and too large for all real-world measurements that lie between the calibration plane 20 and the X-ray source 4. However, for some applications, it may yield sufficiently accurate results. For example, a calibration plane 20 parallel to the plane of the detector plate 6 and through the center of the femoral head will yield a scaling factor SPD/SDD that is acceptable for measuring the diameter of the femoral head or the diameter of the acetabulum. In all of the following approaches, a measurement of the diameter of a circle (e.g. the depiction of a substantially spherical anatomical part, such as the femoral head or the acetabulum) can be adequately corrected by applying a scaling factor appropriate for the center of the circle.

For more complex measurements, e.g. distances between landmark points at substantially varying distances from the plane of the detector plate 6, a calibration plane 20 that is not parallel to the plane of the detector plate 6 may be determined. Each point in the calibration plane 20 will lie at a different perpendicular distance PDD from the plane of the detector plate 6, and, accordingly, will have a different SPD=SDD−PDD.

The ratio SPD/SDD can then be used to compute a range for scaling instead of a fixed value by creating fuzzy measurements and, in the exemplary application of 2-D templating, fuzzy template proposals. A fuzzy measurement is a range instead of a singular value. For example: if a measurement is taken between two anatomical landmarks 14, an SPD can be calculated for each anatomical landmark 14. The depictions of the anatomical landmarks 14 in X-ray image 8 can be back-projected onto calibration plane 20, and the SPD can be determined as described above for each of the resulting corresponding points of calibration plane 20. Each such SPD would result in a different scale factor SPD/SDD. A distance measured between the depictions of two anatomical landmarks 14 in the X-ray image 8 can be translated to a real-world distance within a range between the measured distance multiplied by the lower of the corresponding scale factors and the measured distance multiplied by the higher of the corresponding scale factors. In the exemplary application of 2-D templating, this range may be used in surgical planning (templating) to propose not just one but a range of possibly appropriate implant sizes.

In certain embodiments, for example, for measurements within a certain body part (e.g. knee, hip), the SPD of the most anterior point (farthest away from the detector plate 6) and the most posterior point (closest to the detector) of the 3-D surface scan image 16 of the body part may be determined. In the same way as described above, both values would yield a corresponding scale factor. The appropriate scale factor for any measurement taken of an internal structure between these most anterior and most posterior points can be assumed to lie between these two scale factors. Instead of delivering one real-world value corresponding to the measurement, a range can be given by multiplying the measurement with the two scale factors. For example, the correct scale factor for the diameter of a femoral head measured on an X-ray image can be assumed to lie between the scale factors determined based on an anterior point and a posterior point on the patient's skin. It must be noted that in other, more crude embodiments, the average of the scale factors determined based on an anterior point and a posterior point on the patient's skin may be used as a single scale factor for all measurements, or only one of the anterior plane and posterior plane may be used to derive a scale factor for all measurements.

In another implementation, a calibration plane 20, not necessarily parallel to the detector plate 6, can be fit through a number of anatomical landmarks 14 of interest (e.g. through the center of the femur head, the greater trochanter and the facies patellaris saddle point). Each pixel in the X-ray image 8 would then correspond to a point on that calibration plane 20 (the intersection of the ray from X-ray source 4 to the image pixel and the calibration plane 20). That point would have a certain distance to the detector plate 6, and therefore a certain scale factor. A measurement taken across a number of pixels in the X-ray image 8 could then be multiplied with the lowest and highest scale factors found among these pixels to produce a range of real-world measurements.

The fuzzy measurements and template proposals information may be provided to the surgeon.

In certain embodiments, the X-ray image 8 can be scaled isometrically by changing the image resolution with a scaling factor that is equal to SPD/SDD, whereby SPD can be determined based on the 3-D surface scan image 16 with any definition as described above. That is, the detector plate 6 determines a particular pixel resolution (e.g. 1 pixel=x mm). The scale factor can be used to change the pixel resolution to allow conversion from pixels to real-world measurements at a distance PDD in front of the detector plate 6 (e.g. where the patient 2 is).

In certain embodiments, the user is presented with a visual representation of the calibration plane 20 in relation to the 3-D surface (e.g. a plane combined with a point cloud or mesh representation from the 3-D surface scan image 16 or a modeled 3-D avatar) and can interactively move, e.g., translate and/or rotate the calibration plane 20 to interactively modify the image measurement to real-world measurement correction performed according to any of the methods described herein, e.g. to modify the scaling factor applied to the X-ray image 8.

Alternatively or additionally, the 3-D surface scan image 16 may be used to correct the pose of the X-ray image 8 in relation to the exact position of the patient 8. For example, if, from the 3-D surface scan image 16, or from an SSM fitted to the 3-D surface scan image 16, it is determined that the leg is internally or externally rotated over x degrees, measurements can be corrected to compensate accordingly. For example, as illustrated in FIGS. 27A-C, a correction factor of 1/cos(x) can be applied to horizontal measurements but not to vertical ones. If, in addition, the leg is flexed at an angle of y degrees with respect to the detector, a correction factor of 1/cos(y) can be applied to vertical measurements. A non-horizontal and non-vertical measurement can be separated into its perpendicular components, after which the corresponding correction factors can be applied to those components.

In certain embodiments, the SPD is not defined as a single number describing the position of a parallel plane to the detector plate 6, but the SPD is variable across the detector plate 6 as the ideal imaging plane is not parallel to the detector plate 6. Hence, the scaling is not performed isometrically but a perspective back-projection is performed that corrects for any pose differences or scaling issues.

Figure 28:
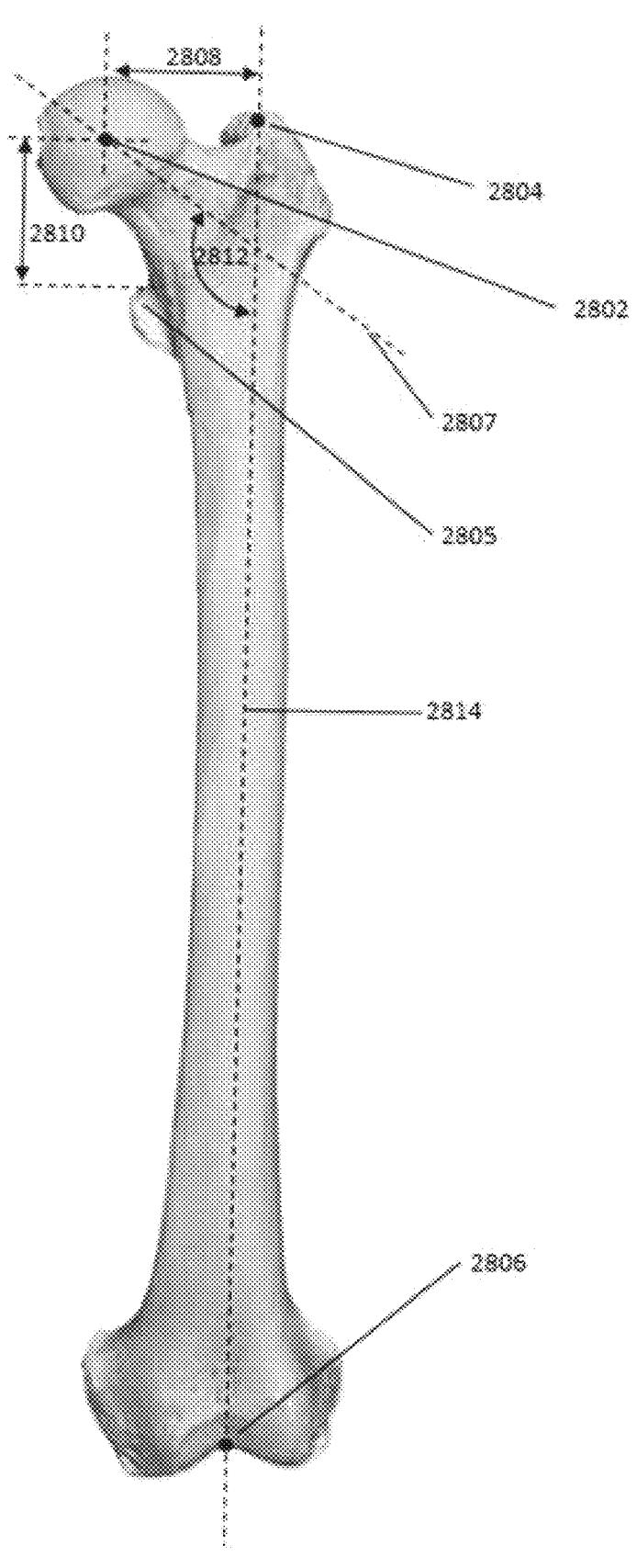
FIG. 28 illustrates an example anatomy structure with identified anatomical landmarks and geometric features thereon for implementation of various embodiments disclosed herein.

For this purpose, a calibration plane 20, not necessarily parallel to the plane of the detector plate 6, can be fit through a number of anatomical landmarks 14 of interest. Each pixel in the X-ray image 8 would then correspond to a point on that calibration plane 20, which can be found by back-projecting the pixel onto the calibration plane 20 (e.g. as the intersection of the ray from the X-ray source 4 to the image pixel and the calibration plane 20). A distance measured between two pixels of X-ray image 8 can then be translated to a distance between two corresponding, back-projected points of calibration plane 20, thus obviating the need for determining a scale factor or for compensating for an incorrect patient pose. For example, the user may wish to perform measurements in the femoral head/neck/shaft plane. Fitting an SSM comprising surface data of the skin and geometrical data relating to certain anatomical landmarks 14 (e.g., with reference to FIG. 28, femoral head or center of femoral head 2802, greater trochanter 2804, lesser trochanter 2805, facies patellaris saddle point 2806, femoral neck axis 2807, femoral shaft axis 2814) may result in approximations of the 3-D positions of said anatomical landmarks. Fitting a calibration plane 20 through those approximative 3-D positions of the center of the femur head 2802, the greater trochanter 2804. and the facies patellaris saddle point 2806 may allow accurate measurements of the femoral neck length, the femoral offset 2808, the vertical offset 2810, the angle 2812 between the femoral neck and the anatomical axis of the femur 2814 and other measurements among anatomical landmarks on the calibration plane 20. This approach will be accurate for measurements between anatomical landmarks 14 that lie on calibration plane 20, but may still yield satisfactory results for measurements between landmarks that lie in the vicinity of calibration plane 20.

Alternatively, in certain embodiments, based on the imaging protocol that includes a 3-D body model and the ideal imaging plane (e.g., the plane of detector plate 6) for measurement, digital templating, or 3-D reconstruction purposes, the physical position of the patient 2 or the components of the imaging system (e.g., X-ray source 4, detector plate 6) may be corrected to ensure obtaining an appropriate imaging plane.

As discussed herein, an imaging protocol is a description given to the radiologist of the kind of image that should be taken. The protocol may include information about imaging settings, pose of the patient, presence of calibration markers 12, etc. Desired pose of the patient 2 is typically described in an imaging protocol in a verbal or qualitative way (e.g. "frontal view of left leg"). If the protocol comprises a 3-D model of a body or body part and a plane representing the detector plate 6 in the desired spatial relationship to each other (e.g. the desired pose of the patient 2 with respect to the plane of detector plate 6), that protocol could be loaded onto a combined 3-D scan/imaging machine, e.g., scanning device 111. The machine, e.g., 3-D scanning device 111b, could intermittently or continuously scan the patient after being positioned by the radiologist. The machine can compare the generated 3-D surface scan image 16 with the 3-D body (part) model, and give feedback. For example, the feedback can be visual, such as by overlaying the 3-D body model and the 3-D surface scan 16 on the screen, by coloring one or both of these depending on how well the desired pose has been achieved, or by showing arrows indicating how the patient 2 should be moved to achieve the desired pose. As another example, the feedback can be auditory, such as by emitting a sound that gets louder as the patient 2 approaches the desired pose, or by emitting intermittent beeps that follow each other faster and faster as the patient 2 approaches the desired pose to help in achieving the desired pose.

In certain embodiments, the 3-D surface scan image may be used to correct geometric imaging artifacts such as image distortion in the X-ray image 8. Image distortion may result from the object of interest not being parallel to the plane of the detector plate 6. This can result in a scaling factor which is different in different regions of the image. The 3-D surface scan image 16 can be used to detect the pose of the object of interest in relation to the detector plate 6 and apply a non-uniform (e.g. linearly varying) scaling factor across the image.

For example, the X-ray image 8 may be acquired with the knee bent in relation to the detector plate 6. This would lead to the femur and tibia not being parallel to the detector plate 6, and in the case of a standing X-ray, a different scaling factor being observed in the resulting X-ray image 8, depending on the craniocaudal position. This image distortion can thus be reversed by determining the correct pose with the 3-D surface scan image 8. For example, appropriate SPDs may be determined for the hip, knee and ankle, each resulting in a scaling factor SPD/SDD. A scaling factor can then be linearly interpolated for all points of X-ray image 8 with a craniocaudal position between the depictions of the hip and knee, from the scaling factor for the hip and the scaling factor for the knee. Similarly, a scaling factor can be linearly interpolated for all points of X-ray image 8 with a craniocaudal position between the depictions of the knee and the ankle, from the scaling factor for the knee and the scaling factor for the ankle.

In certain embodiments, one or more X-ray images 8 may be calibrated and reconstructed, in combination with the corresponding one or more 3-D surface scan image 16 and a population model (e.g. a statistical shape model), to one or multiple 3-D models of the internal (e.g., bony) anatomy 10 of the patient 2.

Reconstructing a patient-specific 3-D shape by fitting an SSM (a specific kind of population model) onto a single X-ray image 8 first may include a calibration of the X-ray image 8. This effectively means determining the scale of what is depicted in the X-ray image 8. As discussed above, this has traditionally been performed using a calibration marker, but this is far from robust, if only because this relies on proper positioning of the calibration marker near the anatomical part of interest. In certain embodiments, an SPD determined from the 3-D surface scan image 16 may be used to determine an appropriate scaling factor. For example, a calibration plane 20 may be determined through the 3-D surface scan image 16 in the vicinity of the anatomical part of interest. Alternatively, one or more anatomical landmarks 14 may be derived from the 3-D surface scan image 16 according to any of the methods described herein, and an SPD may be determined based on the locations of these anatomical landmarks 14.

Reconstructing a patient-specific 3-D shape by fitting an SSM onto multiple X-ray images 8 first may include a determination of the spatial arrangement of the respective X-ray sources 4 and detector plates 6 of the X-ray images 8 in a single coordinate system (e.g. with respect to an imaged subject that is fixed in space). This is referred to as registering the X-ray images 8. As discussed above, X-ray image registration has traditionally been performed using an elaborate calibration marker, but this is far from robust (if only because between image acquisitions the elaborate calibration marker could move with respect to the patient 2). According to embodiments, the 3-D surface scan images 16 of the patient 2, or parts of those 3-D surface scan images 16 surrounding the internal structure of interest can be used to perform the registration.

Each X-ray image 8 is generated with a corresponding 3-D surface scan image 16. Optionally, in each 3-D surface scan image 16, the part closest to the internal structure of interest is isolated. The 3-D surface scan images 16 or the isolated parts are registered on top of each other (e.g. using an iterative closest point approach). The corresponding X-ray images 8 (e.g. their X-ray sources 4 and detector plates 6) follow the 3-D transformations (e.g. translation, rotation, possibly scaling) of the 3-D surface scan images to bring the X-ray images 8 into the same coordinate system. An SSM representing the 3-D shape of the internal structure of interest can then be fit onto the now-registered X-ray images 8 using any suitable SSM fitting techniques known in the art.

Optionally, an SSM that also comprises the 3-D shape of the skin surrounding the internal structure of interest can be used to perform a combined fitting of the 3-D shape of the internal structure onto the one or more X-ray images 8 and the 3-D shape of the skin onto one or more of the 3-D surface scan images 16. This may improve the accuracy of the 3-D reconstruction of the internal structure. As described above, the 3-D surface scan images 16 may first be used as an intermediary to perform registration of the X-ray images 8.

In certain embodiments, the SPD or any derived anatomical landmarks 14 from the 3-D scan may also be used to create a probabilistic 3-D reconstruction from one or more X-ray images 8, whereby the X-ray scaling is used as a probabilistic range rather than a fixed value.

In certain embodiments, the user is presented with a visual representation of the X-ray calibration plane 20 in relation to the 3-D surface (e.g. a plane combined with a point cloud or mesh representation of the 3-D surface scan image 16 or a modeled 3-D avatar) and can interactively move the calibration plane to interactively modify the scaling factor applied to the information retrieved from the X-ray image 8. When reconstructing a 3-D shape from multiple X-ray images 8, a visual representation of one calibration plane 20 per X-ray image 8 can be presented to the user.

In certain embodiments, the size of the patient 2 in relation to a probabilistic model of anatomical landmarks 14 may be used to modify the scaling factor used for reconstruction based on the projected source-landmark distance (SLD). As an example, based on a statistical model and the 3-D surface scan image 16, the position of the acetabular hip center and femoral head center in relation to the detector plate 6 may be estimated. If more than one anatomical landmark 14 is so available, the SLD information may be used to apply a different scaling factor to different parts of the anatomy 10 during 3-D reconstruction.

As discussed herein, the SLD is the distance between the X-ray source 4 and a plane parallel to the detector plate 6 and going through an anatomical landmark 14 (e.g. the hip center) inside the patient and can be used for any scaling purposes described herein in the same was as SPD. The SLD could also be the distance between the X-ray source 4 and a plane parallel to the detector plate 6 and through a virtual landmark representing the center of gravity of several anatomical landmarks 14 (e.g. the center point between the hip centers).

The SLD could be determined for several (sets of) anatomical landmarks 14. For example, SLD_1 could be for the left hip center and SLD_2 could be for the center of the left femoral condyles.

Figure 11:
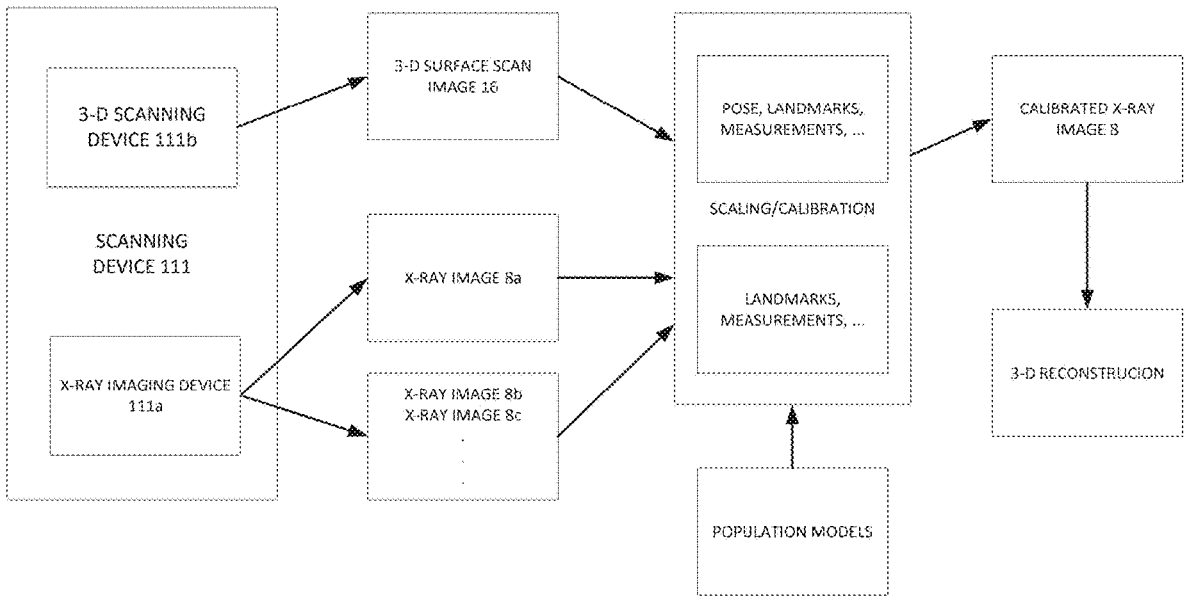
FIG. 11 is a general example workflow performed in accordance with various embodiments disclosed herein.

A general example workflow performed in accordance with embodiments is shown in FIG. 11. As discussed herein, scanning device 111 generates one or more X-ray images 8a, 8b, 8c, etc. of anatomy 10 of interest of a patient 2 with X-ray imaging device 111a. For each X-ray image, the scanning device 111 concurrently, (or at least with the patient not moving) generates a 3-D surface scan image 16 with the 3-D scanning device 111b. The 3-D scanning device 111b has a known spatial relationship to the X-ray imaging device 111a such that an appropriate transformation of the images into a common coordinate system can be accomplished. Scaling and/or calibration of the X-ray is performed based on information from the 3-D surface scan image 16, such as the pose of the patient 2, anatomical landmarks 14, measurements, and the like. Anatomical landmarks 14, measurements and the like from the X-ray images 8 may also be utilized for scaling and/or calibration of the X-ray images 8. Based on the calibrated X-ray images 8, an accurate 3-D model can be generated.

FIGS. 12-21 and 26 are example methods implementing various aspects of certain embodiments discussed herein. As will be appreciated, the methods may be implemented using any suitable hardware such as scanning device 111 (with X-ray imaging device 111a and 3-D scanning device 111b provided together in an integrated device or provided separately) operating in computer environment 100. The various hardware components may be standard hardware components configured—as specifically designed hardware components, via suitable software, or some combination thereof—to perform the methods disclosed herein.

Figure 12:
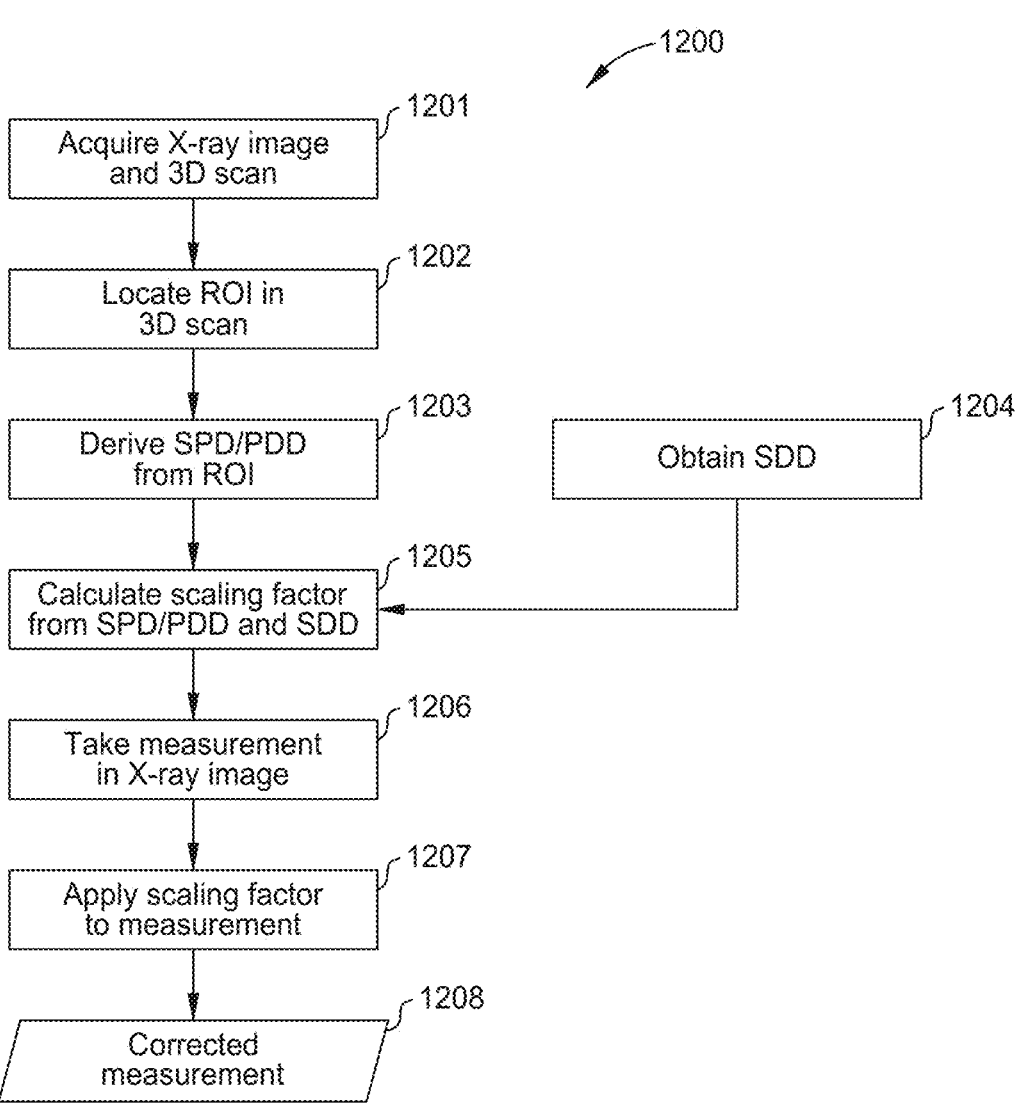
FIG. 12 is an example method of calculating a scaling factor for measurements from an X-ray image according to certain embodiments discussed herein.

FIG. 12 is an example method 1200 of calculating a scaling factor for measurements from an X-ray image according to certain embodiments discussed herein. In step 1201, an X-ray image 8 and a 3-D surface scan image 16 are acquired. In step 1202, a region of interest (ROI) is identified in the 3-D surface scan image 16. In step 1203, the source-patient distance (SPD), patient-detector distance (PDD) and the ratio of SPD/PDD are determined based on the identified ROI. In step 1204, the source-detector distance (SDD) is obtained. In step 1205, a scaling factor is calculated from the SPD/PDD ratio and SDD. In step 1206, a measurement is taken from the X-ray image 8. In step 1207, the scaling factor is applied to the measurement. In step 1208, a corrected measurement is obtained based on the measurement taken from the X-ray image 8 and the applied scaling factor.

Figure 13:
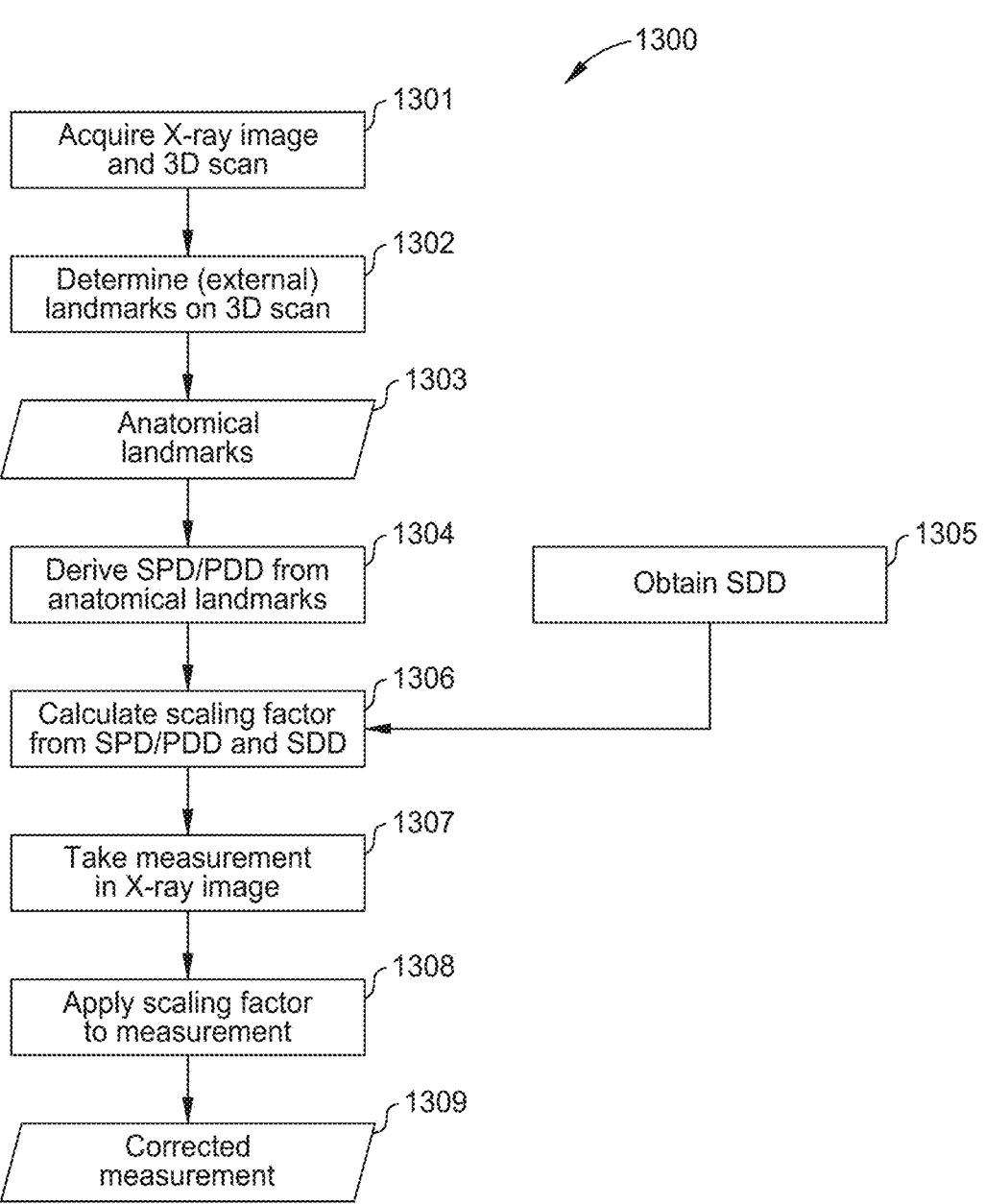
FIG. 13 is another example method of calculating a scaling factor for measurements from an X-ray image according to certain embodiments discussed herein.

FIG. 13 is another example method 1300 of calculating a scaling factor for measurements from an X-ray image according to certain embodiments discussed herein. In step 1301, an X-ray image 8 and a 3-D surface scan image 16 are acquired. In step 1302, external anatomical landmarks are determined on the 3-D surface scan image 16. In step 1303, the position of the determined anatomical landmarks relative to the X-ray source 4 and detector plate 6 is determined. In step 1304, SPD, PDD and the ratio SPD/PDD are derived from the determined position of the anatomical landmarks. In step 1305, SDD is obtained. In step 1306, a scaling factor is calculated from the SPD/PDD ratio and SDD. In step 1307, a measurement is taken from the X-ray image 8. In step 1308, the scaling factor is applied to the measurement. In step 1309, a corrected measurement is obtained based on the measurement taken from the X-ray image 8 and the applied scaling factor.

Figure 14:
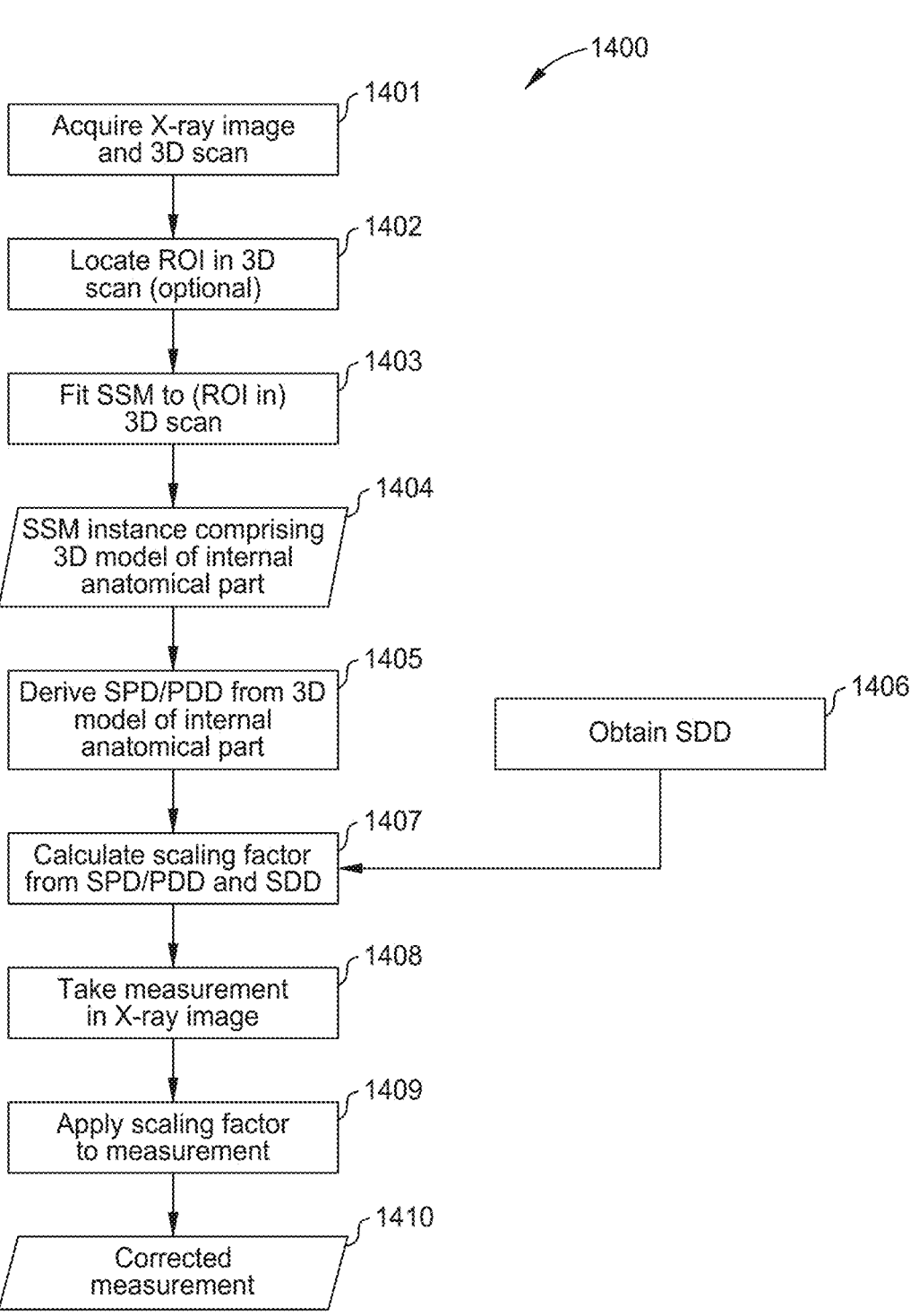
FIG. 14 is an example method of calculating a scaling factor for measurements from an X-ray image according to certain embodiments discussed herein.

FIG. 14 is another example method 1400 of calculating a scaling factor for measurements from an X-ray image according to certain embodiments discussed herein. In step 1401, an X-ray image 8 and a 3-D surface scan image 16 are acquired. In optional step 1402, a region of interest (ROI) is identified in the 3-D surface scan image 16. In step 1403, a statistical shape model is fit to the 3-D surface scan image 16, and optionally to the ROI identified in the 3-D surface scan image 16. In step 1404, a statistical shape model (SSM) instance comprising a 3-D model of an internal anatomical part, optionally corresponding to the ROI, is provided. In step 1405, SPD, PDD and the ratio SPD/PDD are derived from the 3-D model of the internal anatomical part. In step 1406, SDD is obtained. In step 1407, a scaling factor is calculated from the SPD/PDD ratio and SDD. In step 1408, a measurement is taken from the X-ray image 8. In step 1409, the scaling factor is applied to the measurement. In step 1410, a corrected measurement is obtained based on the measurement taken from the X-ray image 8 and the applied scaling factor.

Figure 15:
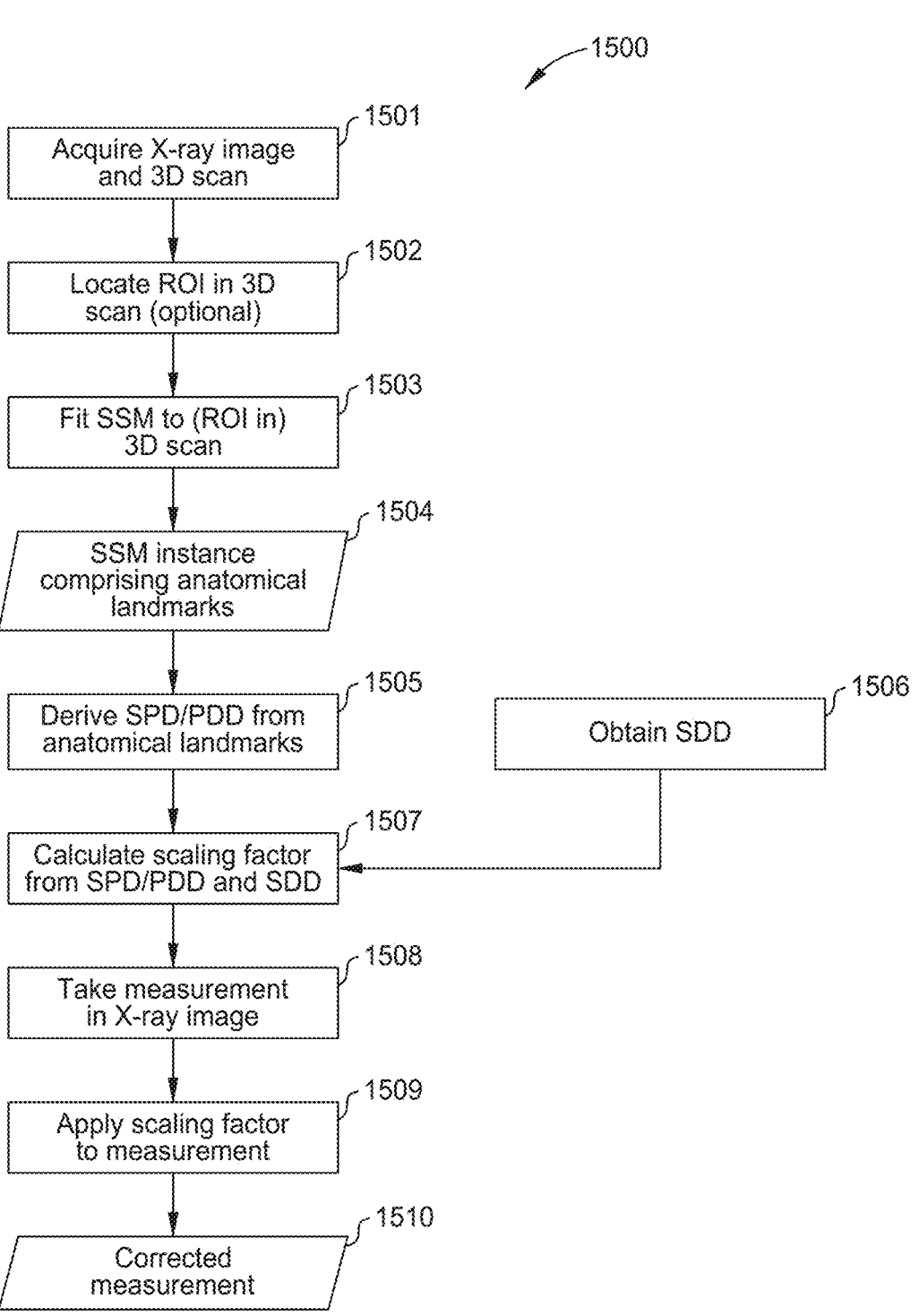
FIG. 15 is another example method of calculating a scaling factor for measurements from an X-ray image according to certain embodiments discussed herein.

FIG. 15 is another example method 1500 of calculating a scaling factor for measurements from an X-ray image according to certain embodiments discussed herein. In step 1501, an X-ray image 8 and a 3-D surface scan image 16 are acquired. In optional step 1502, a region of interest (ROI) is identified in the 3-D surface scan image 16. In step 1503, a statistical shape model is fit to the 3-D surface scan image 16, and optionally to the ROI identified in the 3-D surface scan image 16. In step 1504, a statistical shape model (SSM) instance comprising anatomical landmarks is provided. In step 1505, SPD, PDD and the ratio SPD/PDD are derived from the anatomical landmarks in the SSM. In step 1506, SDD is obtained. In step 1507, a scaling factor is calculated from the SPD/PDD ratio and SDD. In step 1508, a measurement is taken from the X-ray image 8. In step 1509, the scaling factor is applied to the measurement. In step 1510, a corrected measurement is obtained based on the measurement taken from the X-ray image 8 and the applied scaling factor.

Figure 16:
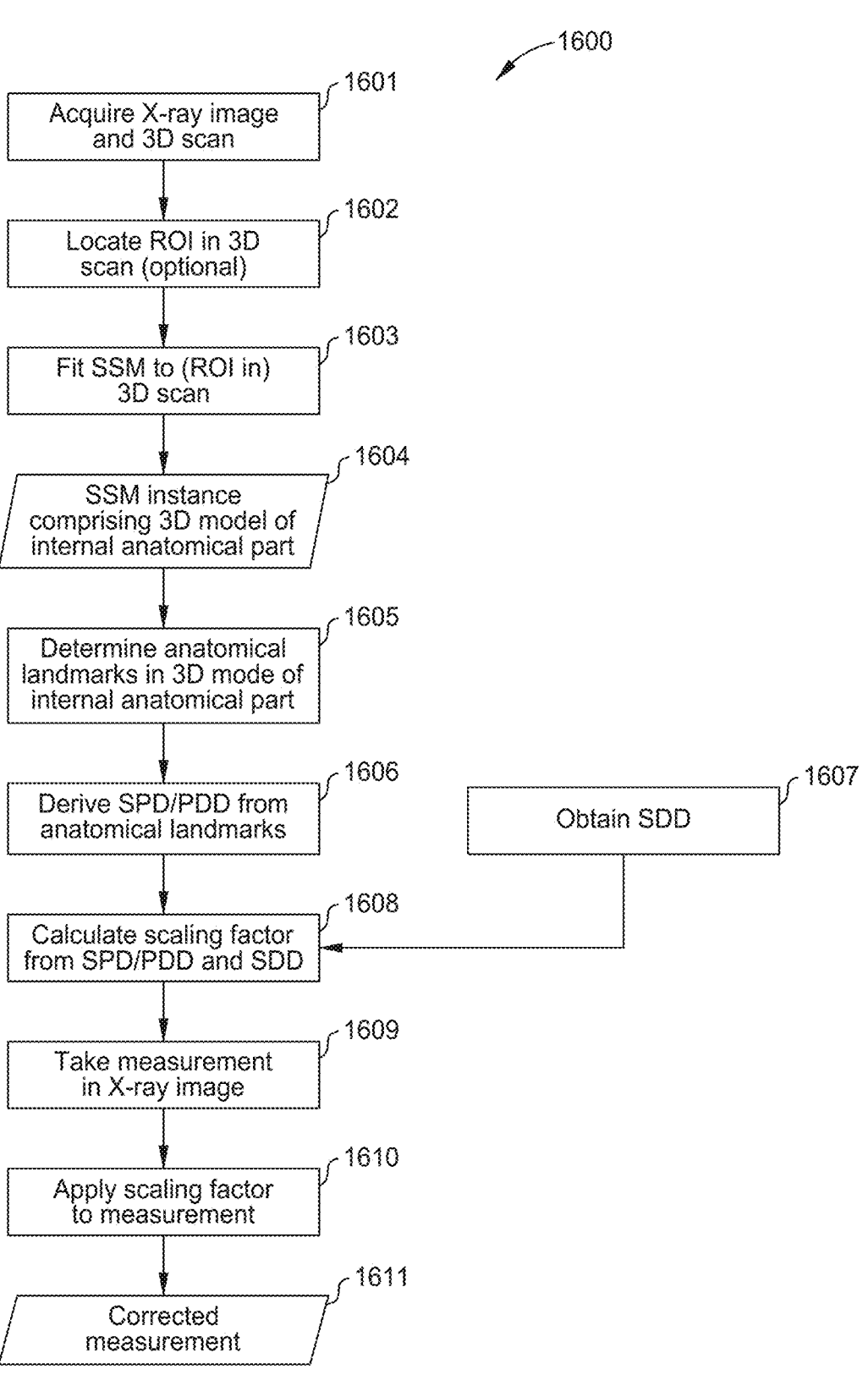
FIG. 16 is another example method of calculating a scaling factor for measurements from an X-ray image according to certain embodiments discussed herein.

FIG. 16 is another example method 1600 of calculating a scaling factor for measurements from an X-ray image according to certain embodiments discussed herein. In step

1601, an X-ray image 8 and a 3-D surface scan image 16 are acquired. In optional step 1602, a region of interest (ROI) is identified in the 3-D surface scan image 16. In step 1603, a statistical shape model is fit to the 3-D surface scan image 16, and optionally to the ROI identified in the 3-D surface scan image 16. In step 1604, a statistical shape model (SSM) instance comprising a 3-D model of an internal anatomical part, optionally corresponding to the ROI, is provided. In step 1605, one or more anatomical landmarks are identified in the 3-D model of the internal anatomical landmark part. In step 1606, SPD, PDD and the ratio SPD/PDD are derived from the one or more anatomical landmarks. In step 1607, SDD is obtained. In step 1608, a scaling factor is calculated from the SPD/PDD ratio and SDD. In step 1609, a measurement is taken from the X-ray image 8. In step 1610, the scaling factor is applied to the measurement. In step 1611, a corrected measurement is obtained based on the measurement taken from the X-ray image 8 and the applied scaling factor.

Figure 17:
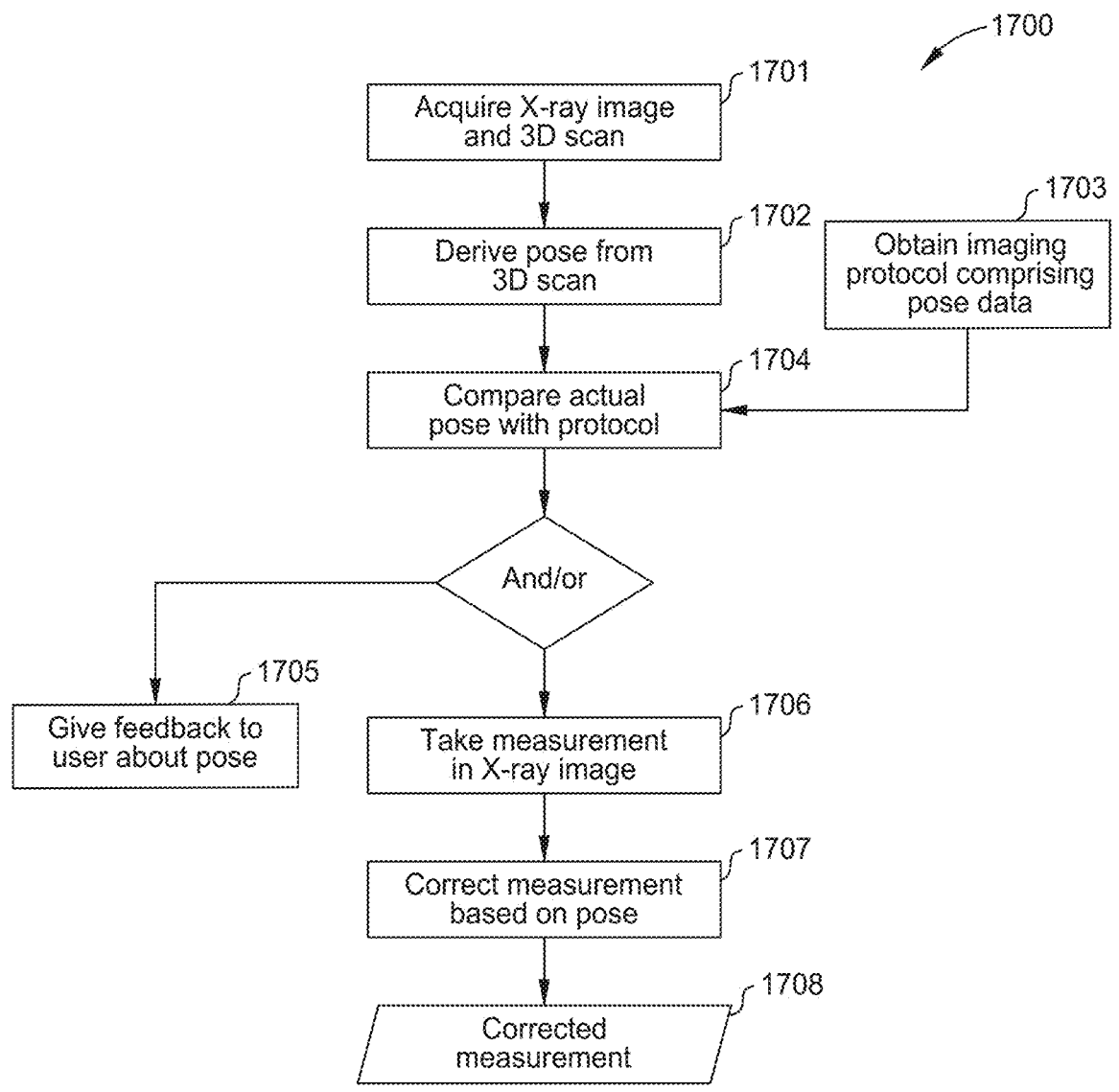
FIG. 17 is an example method of analyzing a pose of a patient in an X-ray to provide feedback and/or correcting measurements from the X-ray according to certain embodiments discussed herein.

FIG. 17 is an example method 1700 of analyzing a pose of a patient in an X-ray to provide feedback and/or correcting measurements from the X-ray according to certain embodiments discussed herein. In step 1701, an X-ray image 8 and a 3-D surface scan image 16 are acquired. In step 1702, a pose of the patient or an anatomical part of the patient is derived from the 3-D surface scan image 16. In step 1703, an imaging protocol comprising pose data is obtained. In step 1704, the derived pose is compared to the imaging protocol. In step 1705, feedback to the patient and/or radiologist regarding the pose is provided. Alternatively or in addition to step 1705, in step 1706, a measurement is taken from the X-ray image 8. In step 1707, a correction to the measurement is applied based on the pose. In step 1708, a corrected measurement is obtained.

Figure 18:
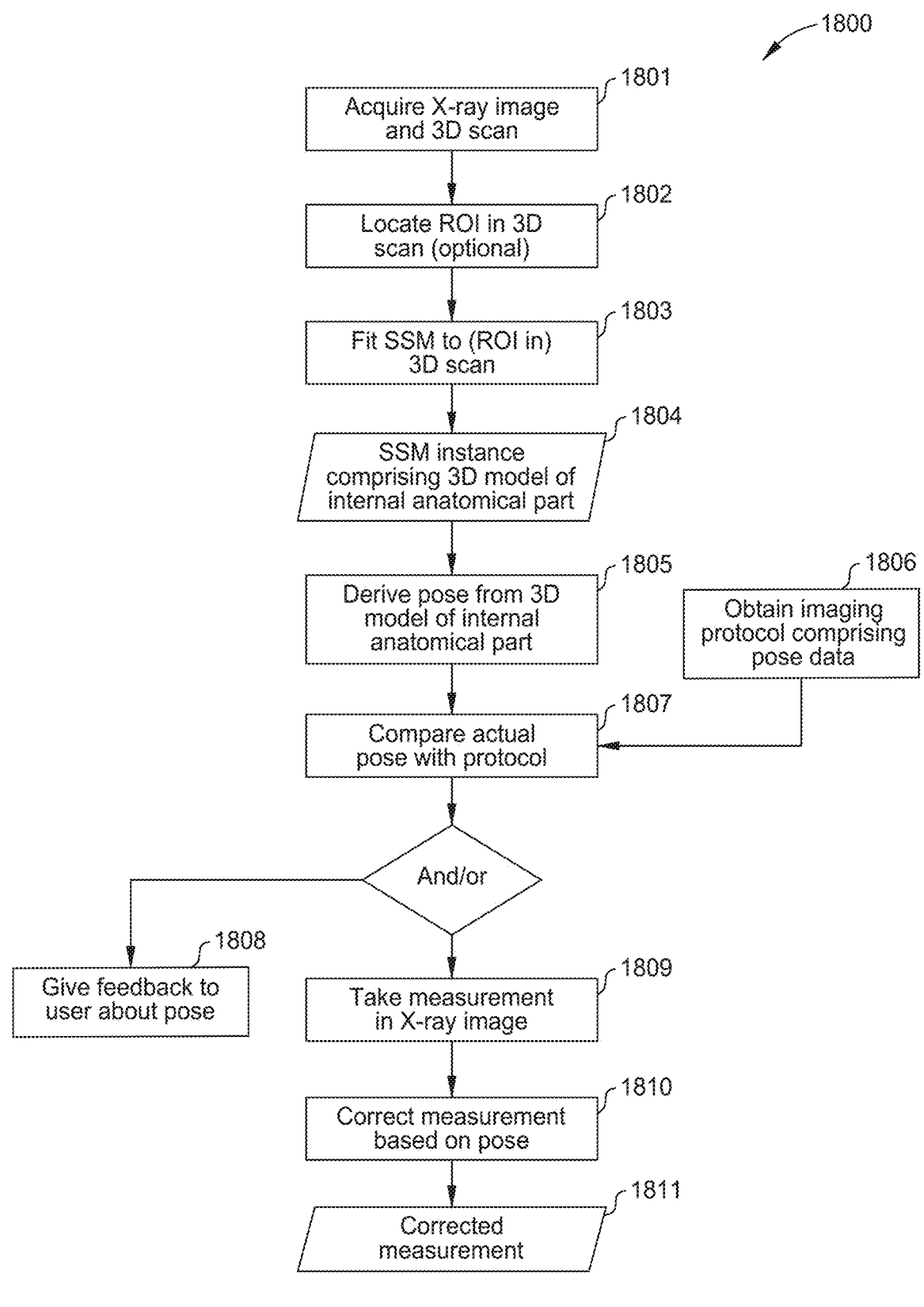
FIG. 18 is another example method of analyzing a pose of a patient in an X-ray to provide feedback and/or correcting measurements from the X-ray according to certain embodiments discussed herein.

FIG. 18 is another example method 1800 of analyzing a pose of a patient in an X-ray to provide feedback and/or correcting measurements from the X-ray according to certain embodiments discussed herein. In step 1801, an X-ray image 8 and a 3-D surface scan image 16 are acquired. In optional step 1802, a region of interest (ROI) is identified in the 3-D surface scan image 16. In step 1803, a statistical shape model is fit to the 3-D surface scan image 16, and optionally to the ROI identified in the 3-D surface scan image 16. In step 1804, a statistical shape model (SSM) instance comprising a 3-D model of an internal anatomical part, optionally corresponding to the ROI, is provided. In step 1805, a pose of the patient or an anatomical part of the patient is derived from the 3-D model. In step 1806, an imaging protocol comprising pose data is obtained. In step 1807, the derived pose is compared to the imaging protocol. In step 1808, feedback to the patient and/or radiologist regarding the pose is provided. Alternatively or in addition to step 1808, in step 1809, a measurement is taken from the X-ray image 8. In step 1810, a correction to the measurement is applied based on the pose. In step 1811, a corrected measurement is obtained.

Figure 19:
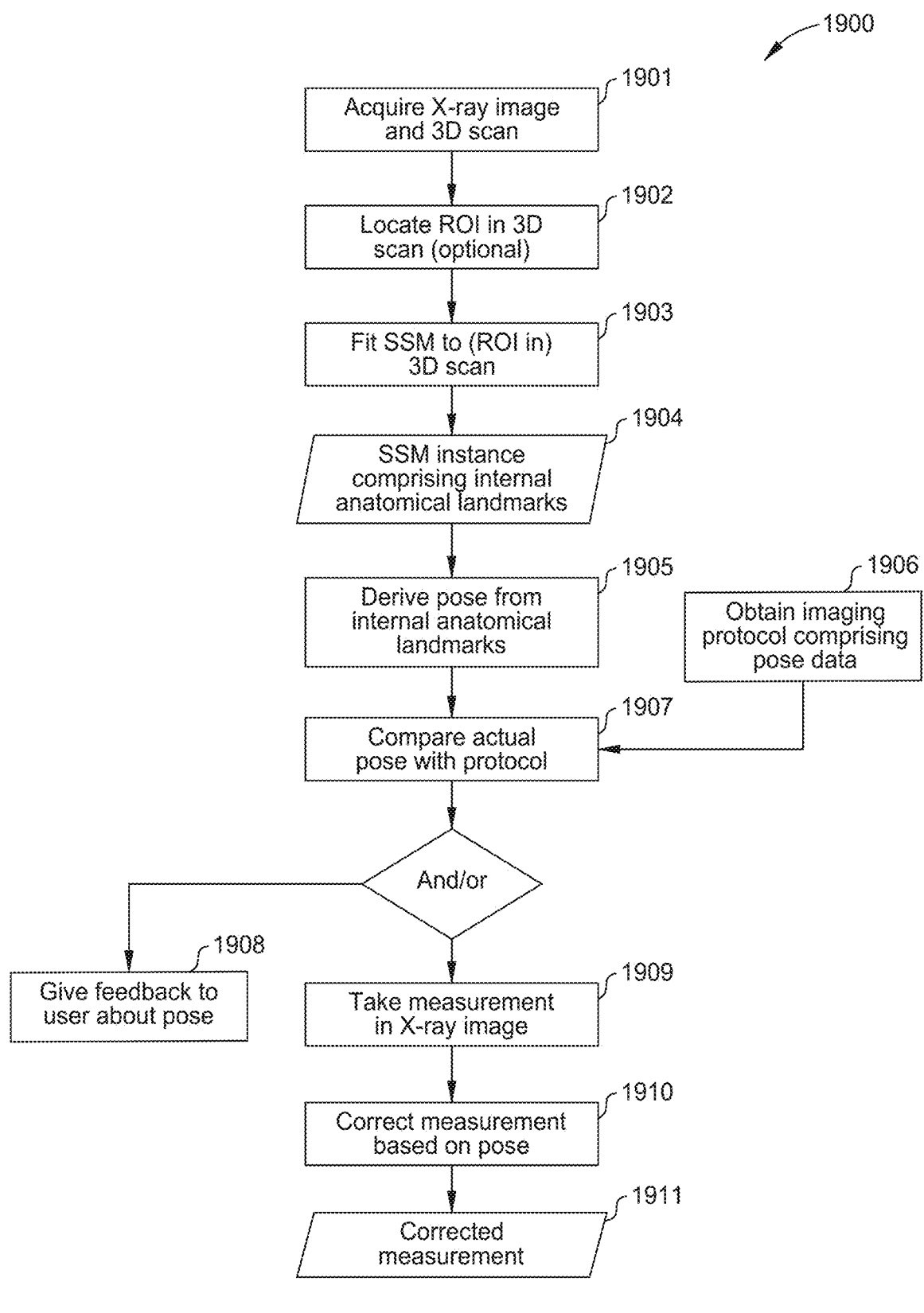
FIG. 19 is another example method of analyzing a pose of a patient in an X-ray to provide feedback and/or correcting measurements from the X-ray according to certain embodiments discussed herein.

FIG. 19 is another example method 1900 of analyzing a pose of a patient in an X-ray to provide feedback and/or correcting measurements from the X-ray according to certain embodiments discussed herein. In step 1901, an X-ray image 8 and a 3-D surface scan image 16 are acquired. In optional step 1902, a region of interest (ROI) is identified in the 3-D surface scan image 16. In step 1903, a statistical shape model (SSM) is fit to the 3-D surface scan image 16, and optionally to the ROI identified in the 3-D surface scan image 16. In step 1904, a statistical shape model (SSM) instance comprising internal anatomical landmarks is provided. In step 1905, a pose of the patient or an anatomical part of the patient is derived from the anatomical landmarks in the SSM. In step 1906, an imaging protocol comprising pose data is obtained. In step 1907, the derived pose is compared to the imaging protocol. In step 1908, feedback to the patient and/or radiologist regarding the pose is provided. Alternatively or in addition to step 1908, in step 1909, a measurement is taken from the X-ray image 8. In step 1910, a correction to the measurement is applied based on the pose. In step 1911, a corrected measurement is obtained.

Figure 20:
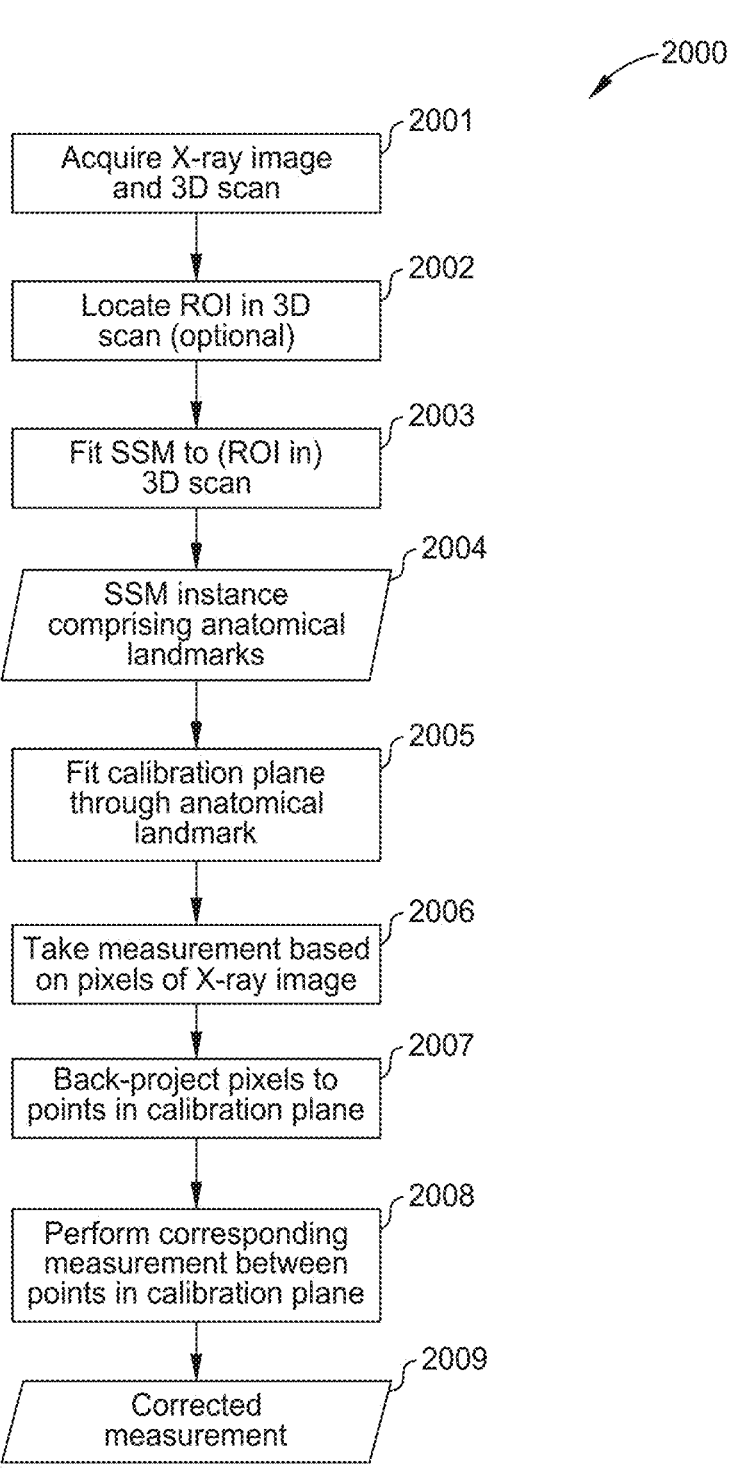
FIG. 20 is an example method of calculating a calibration plane for correcting measurements from an X-ray image according to certain embodiments discussed herein.

FIG. 20 is an example method 2000 of calculating a calibration plane for correcting measurements from an X-ray image according to certain embodiments discussed herein. In step 2001, an X-ray image 8 and a 3-D surface scan image 16 are acquired. In optional step 2002, a region of interest (ROI) is identified in the 3-D surface scan image 16. In step 2003, a statistical shape model (SSM) is fit to the 3-D surface scan image 16, and optionally to the ROI identified in the 3-D surface scan image 16. In step 2004, a statistical shape model (SSM) instance comprising anatomical landmarks is provided. In step 2005, a calibration plane is fit through the anatomical landmarks in the SSM. In step 2006, a measurement is taken based on pixels in the X-ray image 8. In step 2007, the pixels are back-projected to corresponding points in the calibration plane. In step 2008, a corresponding measurement is taken between the back-projected points in the calibration plane. In step 2009, a corrected measurement is obtained based on the measurement taken in the calibration plane.

Figure 21:
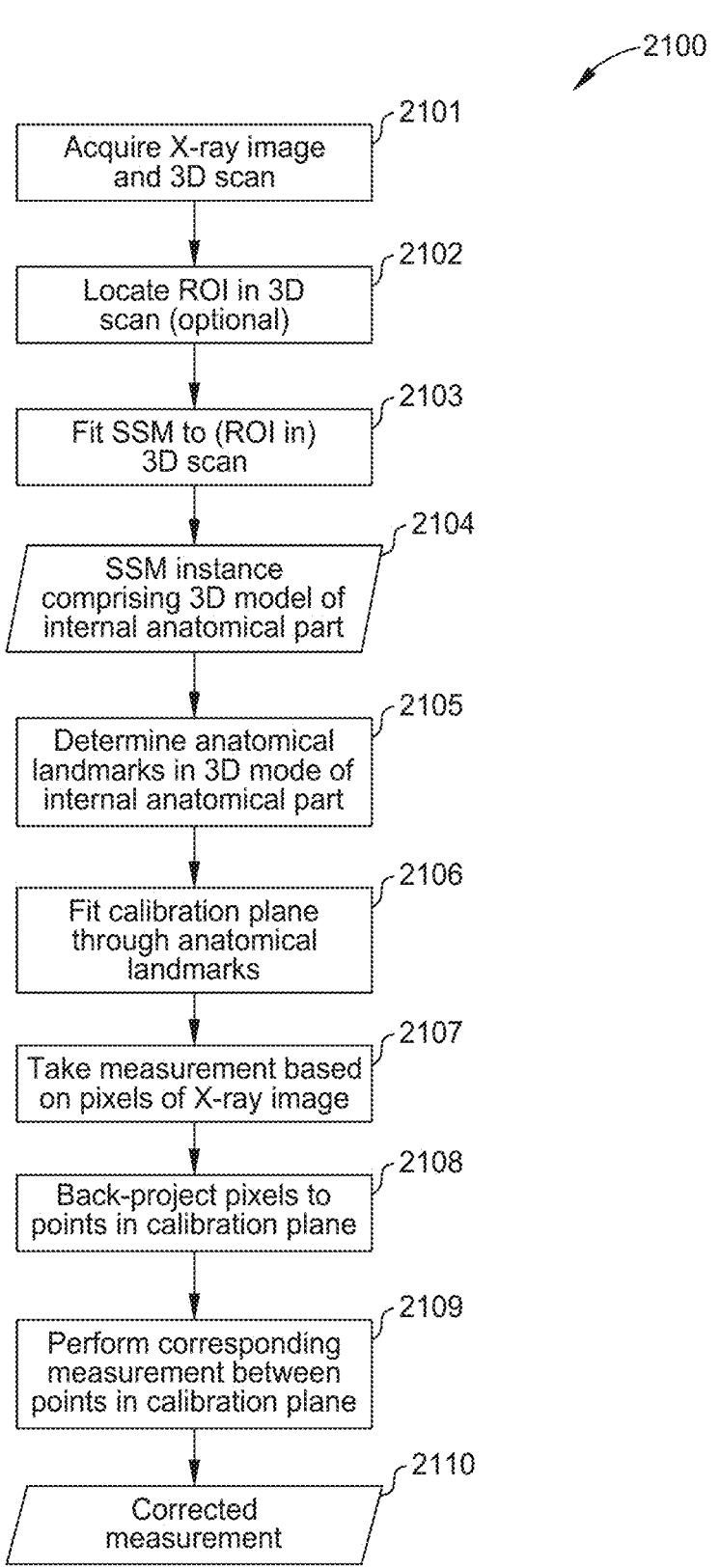
FIG. 21 is an example method of calculating a calibration plane for correcting measurements from an X-ray image according to certain embodiments discussed herein.

FIG. 21 is another example method 2100 of calculating a calibration plane for correcting measurements from an X-ray image according to certain embodiments discussed herein. In step 2101, an X-ray image 8 and a 3-D surface scan image 16 are acquired. In optional step 2102, a region of interest (ROI) is identified in the 3-D surface scan image 16. In step 2103, a statistical shape model (SSM) is fit to the 3-D surface scan image 16, and optionally to the ROI identified in the 3-D surface scan image 16. In step 2104, a statistical shape model (SSM) instance comprising a 3-D model of an internal anatomical part, optionally corresponding to the ROI, is provided. In step 2105, anatomical landmarks are determined from the 3-D model. In step 2106, a calibration plane is fit through the anatomical landmarks in the SSM. In step 2107, a measurement is taken based on pixels in the X-ray image 8. In step 2108, the pixels are back-projected to corresponding points in the calibration plane. In step 2109, a corresponding measurement is taken between the back-projected points in the calibration plane. In step 2110, a corrected measurement is obtained based on the measurement taken in the calibration plane.

Example Applications According to Certain Embodiments

Embodiments discussed herein may be used, in certain embodiments, to implement calibration of X-ray images 8 for THA, TKA, TSA, trauma, spine, CMF templating purposes to be implemented without the use of a calibration element 12.

Embodiments discussed herein may be used, in certain embodiments, to implement the generation of a 3-D model of the anatomy for 3-D pre-operative planning purposes based on one or more X-ray images 8. Examples regarding 3-D model reconstruction based on one or more X-ray images 8, optionally in combination with the 3-D surface scan image 16 are described above.

Embodiments discussed herein may be used, in certain embodiments, to implement feedback with the templating software to surgeons on the limb positioning and foot/leg positioning of the patient 8 when generating the X-ray image 8. Examples regarding including the 3-D surface scan image 16 into the imaging protocol are described above.

Embodiments discussed herein may be used, in certain embodiments, to implement 3-D femoral rotation estimate in templating software. Several examples of internally or externally rotated femur and negative consequences on accuracy of measurements are discussed above.

Embodiments discussed herein may be used, in certain embodiments, to create instruments for surgical guidance based on the body contours or other surfaces acquired using the 3-D surface scan image 16, e.g. for ankle, forearm, spine, CMF. These instruments may also be created for obtaining percutaneous biopsies, e.g. for cancer, whereby the target biopsy location is determined on an X-ray image 8 and the guide is created based on the 3-D surface scan image 16. That is, the combination of the X-ray image 8 and 3-D surface scan image 16 can be used to create a biopsy guide.

For bone- or cartilage-supported devices, the design part of the process (the step from 3-D anatomy model and surgical plan to device design) is unchanged, but certain embodiments described herein can improve the part of the process leading to a 3-D model of the (bone or cartilage) anatomy used as input for designing the device. Rather than obtaining a 3-D anatomy model by segmenting medical images (e.g. CT or MRI scans), the methods described here would allow a 3-D reconstruction based on one or more X-ray images 8. Such a 3-D reconstruction was possible before, but now it is made more robust/accurate by using the 3-D surface scan image 16 instead of a calibration marker 12 to determine an appropriate scale factor for each X-ray image 8 (e.g., determine PDD/SPD) and to register the different X-ray images 8 to each other in a single coordinate system.

For soft-tissue supported devices, such as skin-supported devices, what changes additionally, is that the 3-D anatomy models can come from different sources. For example, 3-D models of internal structures that are needed for creating a surgical plan and a design for any functional elements (such as drill cylinders) can come from a 3-D reconstruction based on one or more X-ray images 8, whereas the 3-D model of the soft tissue (e.g. skin) that is needed to design the anatomy-contacting surface of a patient-specific device (e.g. surgical guide) can come straight from the 3-D surface scan image 16.

The 3-D anatomy models, patient-specific implants and/or surgical guides based on the calibrated X-ray images described herein may be manufactured utilizing various additive manufacturing and/or three-dimensional (3D) printing systems and techniques. Typically, additive manufacturing techniques start from a digital representation of the 3D object to be formed. Generally, the digital representation is divided into a series of cross-sectional layers, or "slices," which are overlaid to form the object as a whole. The layers represent the 3D object, and may be generated using additive manufacturing modeling software executed by a computing device. For example, the software may include computer-aided design and manufacturing (CAD/CAM) software. Information about the cross-sectional layers of the 3D object may be stored as cross-sectional data. An additive manufacturing (e.g. 3D printing) machine or system utilizes the cross-sectional data for the purpose of building the 3D object on a layer by layer basis. Accordingly, additive manufacturing allows for fabrication of 3D objects directly from computer generated data of the objects, such as computer aided design (CAD) files or STL files. Additive manufacturing provides the ability to quickly manufacture both simple and complex parts without tooling and without the need for assembly of different parts.

Additive manufacturing processes generally include providing energy from an energy source (e.g. a laser, an electron beam, etc.) to solidify (e.g. polymerize) layers of building material (e.g. plastic, metal, etc.). For example, the additive manufacturing machine may selectively apply energy from an energy source to (e.g. scan) the building material based on a job file. The job file may include information regarding slices of a digital representation of an object to be built using an additive manufacturing process.

An additive manufacturing machine builds an object on a layer-by-layer basis by applying energy to (e.g. scanning) the layers of building material according to the scanning pattern for each individual layer as indicated in a job file. For example, the additive manufacturing machine may scan a first layer of physical building material corresponding to a first slice of a digital representation of an object according to the scanning pattern for the first slice. The additive manufacturing machine may then scan a second layer of building material corresponding to a second slice adjacent to the first slice according to the scanning pattern for the second slice. The additive manufacturing machine continues scanning layers of building material corresponding to all the slices in the job file, until the layer corresponding to the last slice is scanned.

Selective laser sintering (LS) is an additive manufacturing technique used for 3D printing objects. LS apparatuses often use a high-powered laser (e.g. a carbon dioxide laser) to "sinter" (e.g. fuse) small particles of plastic, metal, ceramic, glass powders, or other appropriate materials into a 3D object. The LS apparatus may use a laser to scan cross-sections on the surface of a powder bed in accordance with a CAD design or job file. Also, the LS apparatus may lower a manufacturing platform by one layer thickness after a layer has been completed and add a new layer of material in order that a new layer can be formed. In some embodiments, an LS apparatus may preheat the powder in order to make it easier for the laser to raise the temperature during the sintering process.

Figure 22:
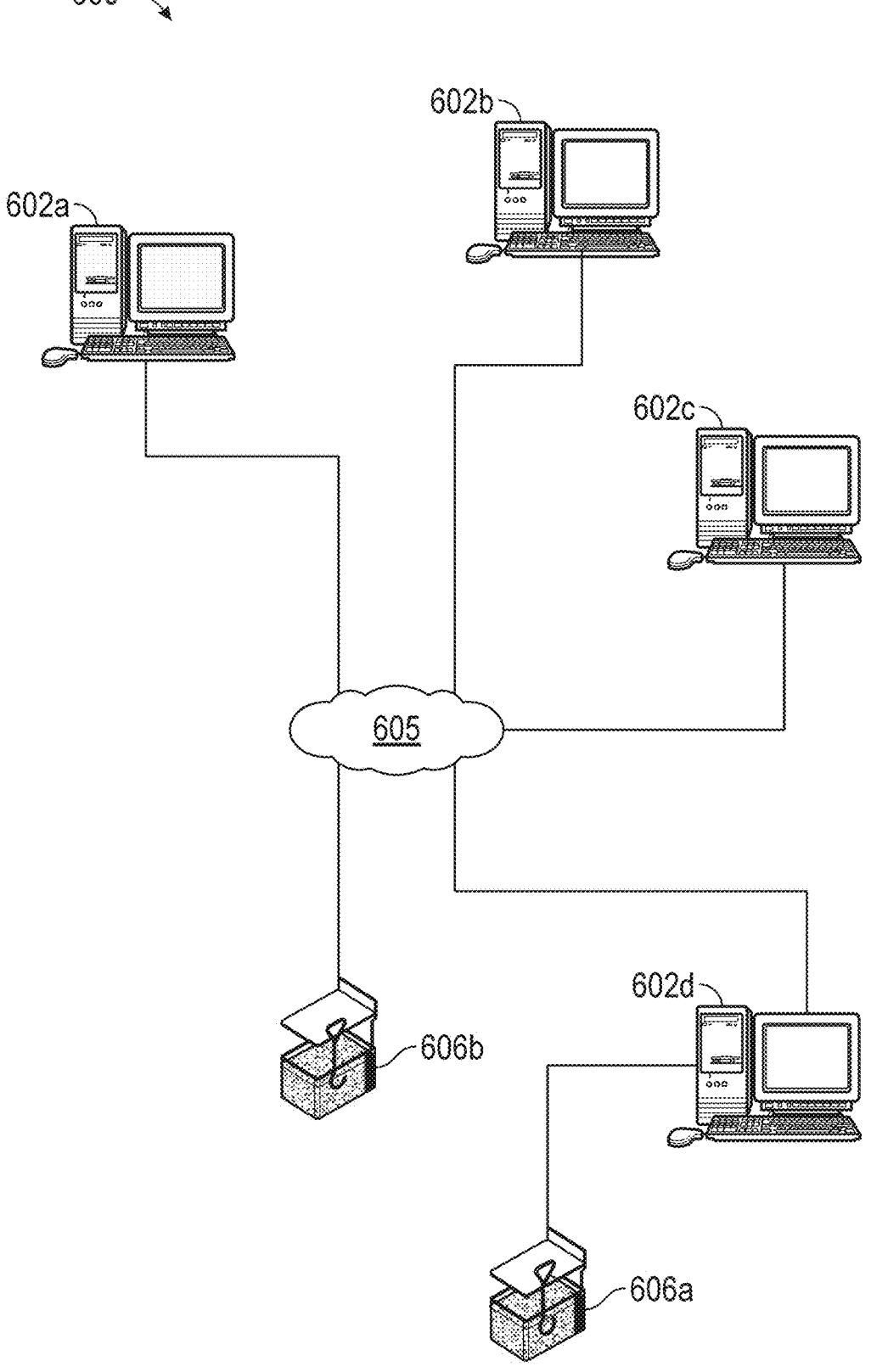
FIG. 22 is an example of a computer environment suitable for the implementation of various embodiments disclosed herein.

Embodiments of the invention, including two-part surgical guides, may be designed and manufactured within a system for designing and manufacturing 3D objects. Turning to FIG. 22, an example of a computer environment suitable for the implementation of 3D object design and manufacturing is shown. The environment includes a system 600. The system 600 includes one or more computers 602a-602d, which can be, for example, any workstation, server, or other computing device capable of processing information. In some aspects, each of the computers 602a-602d can be connected, by any suitable communications technology (e.g. an internet protocol), to a network 605 (e.g. the Internet). Accordingly, the computers 602a-602d may transmit and receive information (e.g. software, digital representations of 3-D objects, commands or instructions to operate an additive manufacturing device, etc.) between each other via the network 605.

The system 600 further includes one or more additive manufacturing devices (e.g. 3-D printers) 606a-606b. As shown the additive manufacturing device 606a is directly connected to a computer 602d (and through computer 602d connected to computers 602a-602c via the network 605) and additive manufacturing device 606b is connected to the computers 602a-602d via the network 605. Accordingly, one of skill in the art will understand that an additive manufacturing device 606 may be directly connected to a computer 602, connected to a computer 602 via a network 605, and/or connected to a computer 602 via another computer 602 and the network 605.

It should be noted that though the system 600 is described with respect to a network and one or more computers, the techniques described herein also apply to a single computer 602, which may be directly connected to an additive manufacturing device 606. Any of the computers 602a-602d may be configured to design and/or manufacture two-part surgical guides as described herein.

Figure 23:
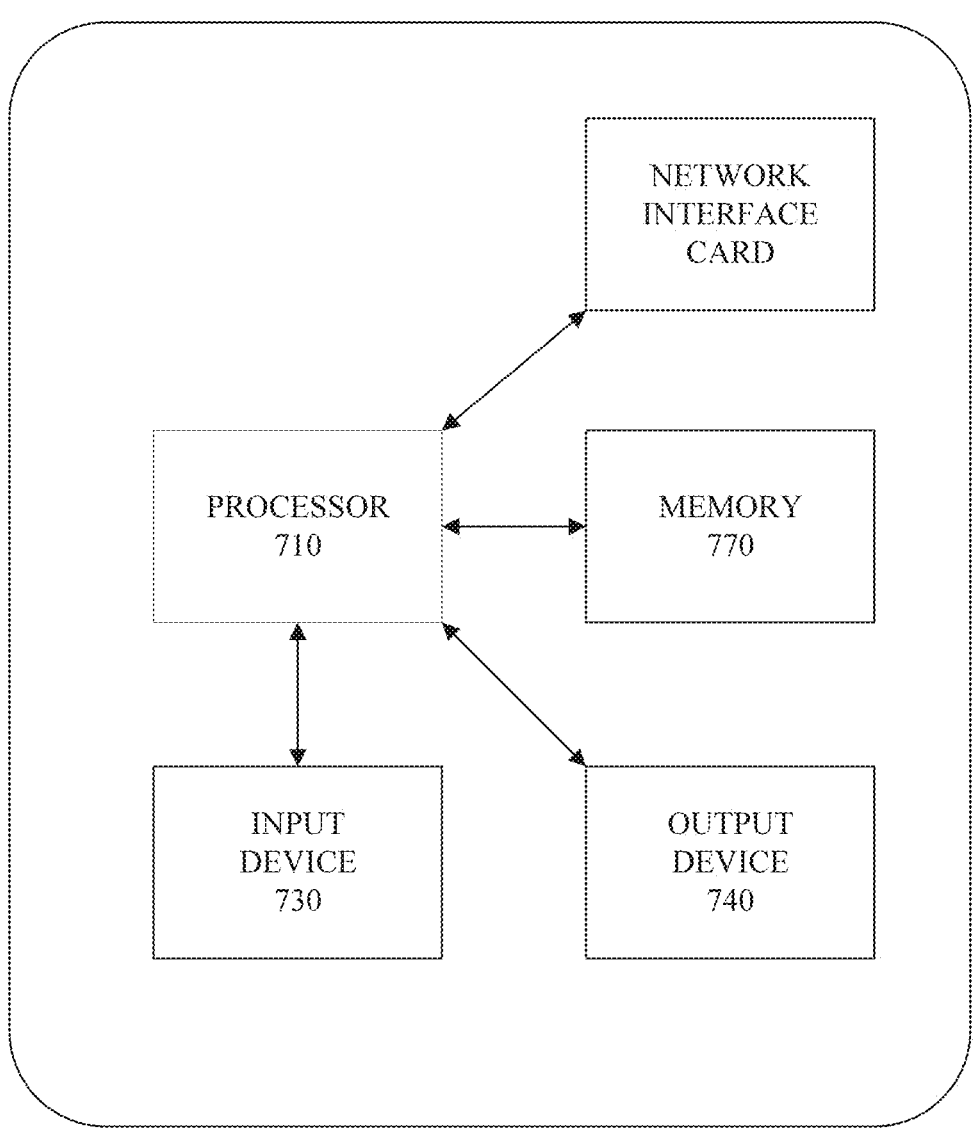
FIG. 23 is a functional block diagram of one example of a computer suitable for use in the computer environment of FIG. 22 for the implementation of various embodiments disclosed herein.

FIG. 23 illustrates a functional block diagram of one example of a computer of FIG. 22. The computer 602a includes a processor 710 in data communication with a memory 720, an input device 730, and an output device 740. In some embodiments, the processor is further in data communication with an optional network interface card 770. Although described separately, it is to be appreciated that functional blocks described with respect to the computer 602a need not be separate structural elements. For example, the processor 710 and memory 720 may be embodied in a single chip.

The processor 710 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g. a combination of a DSP and a microprocessor, a plurality of microprocessors, one or more microprocessors in conjunction with a DSP core, or any other such configuration.

The processor 710 can be coupled, via one or more buses, to read information from or write information to memory 720. The processor may additionally, or in the alternative, contain memory, such as processor registers. The memory 720 can include processor cache, including a multi-level hierarchical cache in which different levels have different capacities and access speeds. The memory 720 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 710 also may be coupled to an input device 730 and an output device 740 for, respectively, receiving input from and providing output to a user of the computer 602a. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g. detect hand gestures or facial gestures), a motion detector, or a microphone (possibly coupled to audio processing software to, e.g. detect voice commands). Suitable output devices include, but are not limited to, visual output devices, including displays and printers, audio output devices, including speakers, headphones, earphones, and alarms, additive manufacturing devices, and haptic output devices.

The processor 710 further may be coupled to a network interface card 770. The network interface card 770 prepares data generated by the processor 710 for transmission via a network according to one or more data transmission protocols. The network interface card 770 also decodes data received via a network according to one or more data transmission protocols. The network interface card 770 can include a transmitter, receiver, or both. In other embodiments, the transmitter and receiver can be two separate components. The network interface card 770, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform certain functions described herein.

Figure 24:
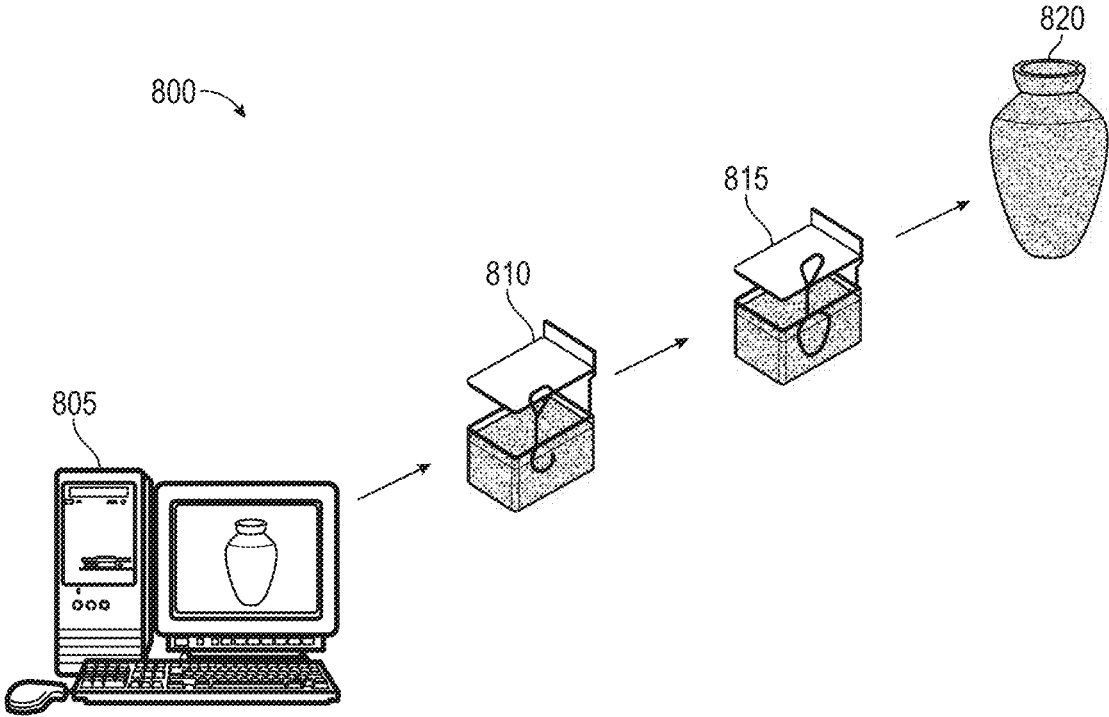
FIG. 24 illustrates an example process for manufacturing a 3-D object or device suitable for the implementation of various embodiments disclosed herein.

FIG. 24 illustrates a process 800 for manufacturing a 3-D object or device. As shown, at a step 805, a digital representation of the object is designed using a computer, such as the computer 602a. For example, 2-D or 3-D data may be input to the computer 602a for aiding in designing the digital representation of the 3-D object. Continuing at a step 810, information is sent from the computer 602a to an additive manufacturing device, such as additive manufacturing device 606, and the device 606 commences the manufacturing process in accordance with the received information. At a step 815, the additive manufacturing device 606 continues manufacturing the 3-D object using suitable materials, such as a liquid resin. At a step 820, the object is finally built.

These suitable materials may include, but are not limited to a photopolymer resin, polyurethane, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC ISO, PC, ULTEM 9085, PPSF and PPSU materials from Stratasys; Accura Plastic, DuraForm, CastForm, Laserform and VisiJet line of materials from 3-Systems; the PA line of materials, PrimeCast and PrimePart materials and Alumide and Car-bonMide from EOS GmbH. The VisiJet line of materials from 3-Systems may include Visijet Flex, Visijet Tough, Visijet Clear, Visijet HiTemp, Visijet e-stone, Visijet Black, Visijet Jewel, Visijet FTI, etc. Examples of other materials may include Objet materials, such as Objet Fullcure, Objet Veroclear, Objet Digital Materials, Objet Duruswhite, Objet Tangoblack, Objet Tangoplus, Objet Tangoblackplus, etc. Another example of materials may include materials from the Renshape 5000 and 7800 series.

Figure 25:
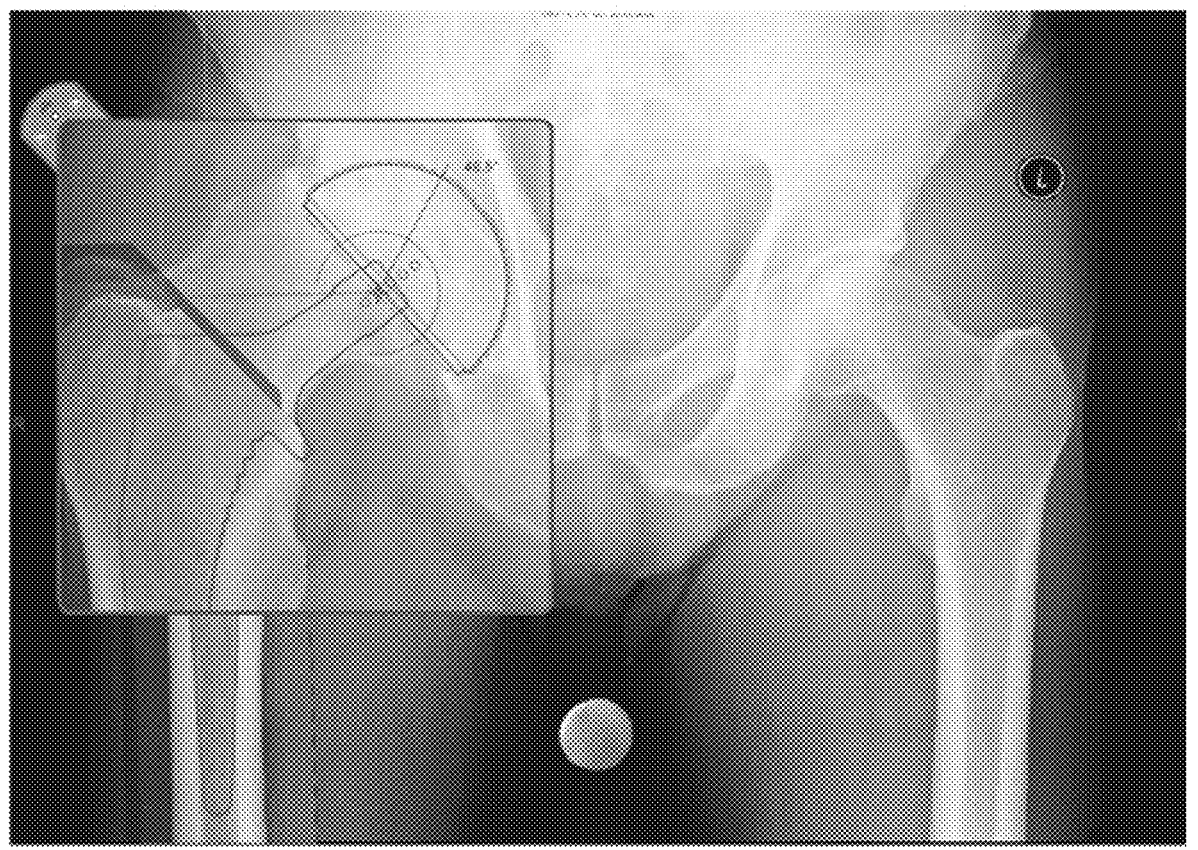
FIG. 25 is an example screen from a graphic user interface in which aspects of certain embodiments discussed herein are implemented.

FIG. 25 is an example screen from a graphic user interface in which aspects of certain embodiments discussed herein are implemented. For example, FIG. 25 illustrates various anatomical landmarks, measurements, geometric features, and proposed implant(s) displayed on an X-ray image 8 that has been calibrated based on a 3-D surface scan image 16 as discussed herein.

Figure 26:
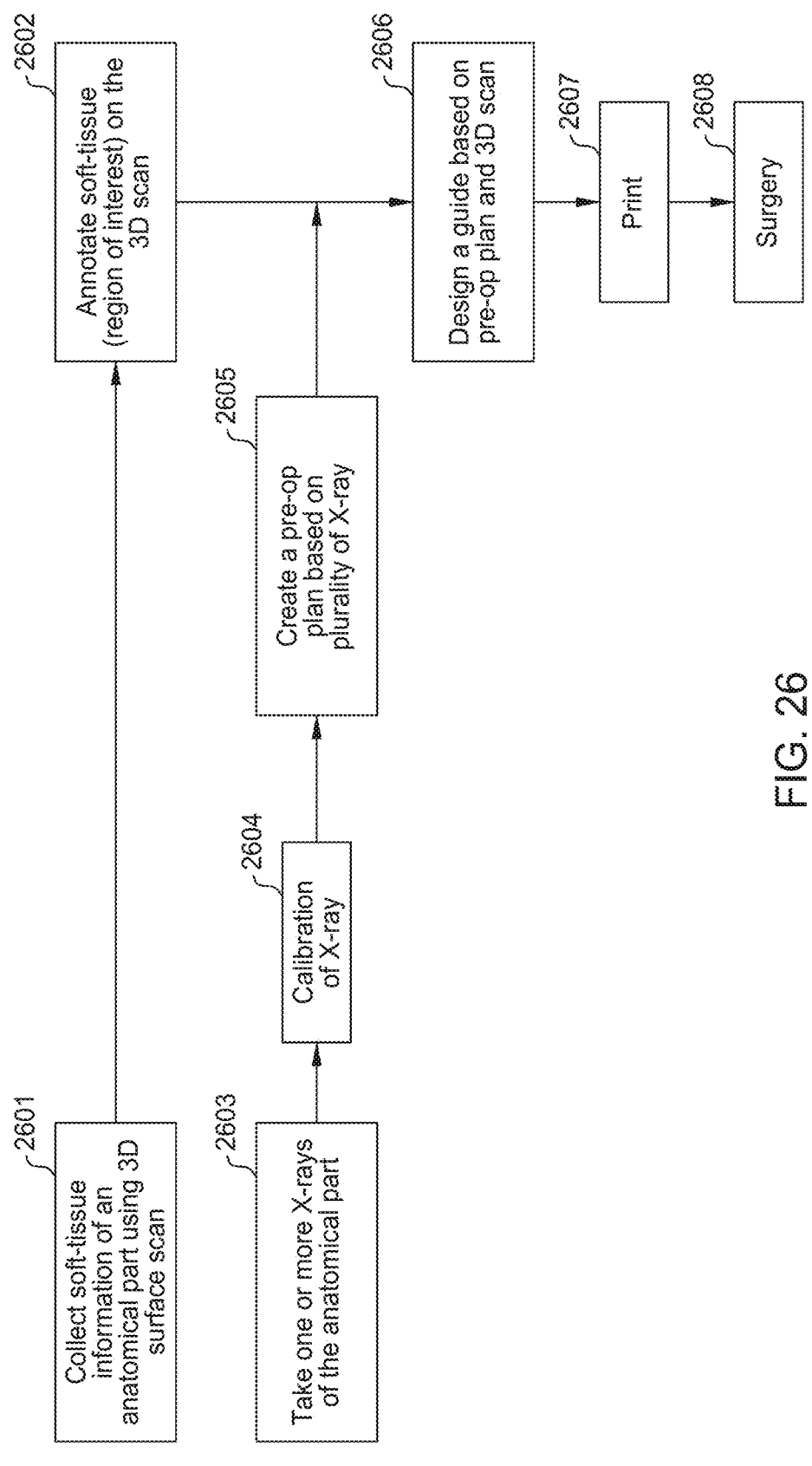
FIG. 26 is an example method of manufacturing a patient-accurate 3-D implant or surgical guide for use in surgery according to certain embodiments disclosed herein.

FIG. 26 is an example method 2600 of using calibration of X-ray images 8 based on the 3-D surface scan image 16 according to certain embodiments discussed herein to manufacture a patient-accurate 3-D implant or surgical guide and use the 3-D implant or surgical guide in surgery. In step 2601, using a 3-D surface scan image 16, soft-tissue information of an anatomical part is collected. In step 2602, a region of interest of soft tissue is annotated on the 3-D surface scan image 16. In step 2603, an X-ray image 8 of the anatomical part is obtained. In step 2604, the X-ray image 8 is calibrated. The X-ray image 8 may be calibrated using a scaling factor or a calibration plane in accordance with certain embodiments discussed herein. In step 26-5, a pre-operation plan is created based on a plurality of calibrated X-ray images 8. In step 2606, an implant or a surgical guide is designed based on the pre-operation plan and the annotated 3-D surface scan image 16. In step 2607, the implant or the surgical guide is additive manufactured/3-D printed based on the design. In step 2608, surgery may be performed using the implant or the surgical guide.

Accordingly, the various embodiments herein solve a technical problem with a technical solution. In particular, one technical problem is that X-rays inherently do not account for the position of the patient with relative to the X-ray source and detector, and therefore the resultant X-ray cannot be relied upon for accurate measurements. This is a technology based problem as taking x-rays inherently requires the use X-ray machines. A technical solution provided by the embodiments is the specific use of a 3-D surface scan to at least one of: determine a scaling factor for the X-ray measurements or an orientation calibration correction. This leads to accurate measurements on an X-ray that improves their use for medical planning and medical procedures. Further, necessarily this requires specialized computerized equipment including 3-D scanners and X-rays, as well as models for registering them which are not capable of being performed in the human mind. The techniques also improve the functionality of automatic measurements taken on X-rays by computing devices as it provides means to account for issues that a computing system normally could not.

Various embodiments disclosed herein provide for the use of a controller or computer control system. A skilled artisan will readily appreciate that these embodiments may be implemented using numerous different types of computing devices, including both general-purpose and/or special-purpose computing-system environments or configurations. Examples of well-known computing systems, environments, and/or configurations that may be suitable for use in connection with the embodiments set forth above may include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like. These devices may include stored instructions, which, when executed by a microprocessor in the computing device, cause the computer device to perform specified actions to carry out the instructions. As used herein, instructions refer to computer-implemented steps for processing information in the system. Instructions can be implemented in software, firmware or hardware and include any type of programmed step undertaken by components of the system.

A microprocessor may be any conventional general-purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special-purpose microprocessor such as a digital signal processor or a graphics processor. The microprocessor typically has conventional address lines, conventional data lines, and one or more conventional control lines.

Aspects and embodiments of the inventions disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

Where aspects and embodiments relate to internal anatomy, such aspects and embodiments have been illustrated with various examples relating to bony anatomy, more particularly from the realm of joint surgery, such as joint replacement. A person skilled in the art will readily appreciate that the disclosed subject matter equally applies, not only to joints but to any type of bony anatomy; to other types of medical treatments on bony anatomy, such as joint resurfacing, corrective osteotomies, bone resection, bone reconstruction, or ligament repair; to other types of internal anatomical parts, such as cartilage, ligaments, muscles, tendons, menisci, teeth, blood vessels, airways and internal organs, such as kidneys, lungs, liver, heart, brain, eyes; and to any other purpose for performing measurements, calibrating X-ray images, registering X-ray images or reconstructing 3-D shapes from X-ray images, such as population analysis, patient analysis, diagnosis, post-treatment analysis, training or mere visualization purposes. Various aspects and embodiments described herein have been illustrated with a human patient. However, a person skilled in the art will readily appreciate that the disclosed subject matter equally applies to animal patients, such as mammals. Various aspects and embodiments described herein have been illustrated with medical examples. However, a person skilled in the art will readily appreciate that the disclosed subject matter equally applies to non-medical, e.g. technical, applications. For example, the subject matter of the present disclosure may be applied to the analysis of internal structures of technical parts. Unless explicitly mentioned otherwise, any methods or method steps disclosed herein may be performed automatically by a computing device, or manually by a user of a computing device. The user may be a medical professional or a non-medical professional, such as a technician or an engineer.

The invention claimed is:

1. A system for calibrating an X-ray image, the system comprising:

at least one memory; and at least one processor coupled to the at least one memory, the at least one processor configured to cause the system to:

receive an X-ray image of an anatomical part of a patient, wherein the X-ray image is obtained by an X-ray imaging device including an X-ray source;

receive a 3-D surface scan of a surface of a portion of the patient where the anatomical part is located, wherein the 3-D surface scan is obtained by a 3-D surface scanning device, wherein the X-ray imaging device and the 3-D surface scanning device are part of a scanning device and have a known spatial relationship between the X-ray imaging device and the 3-D surface scanning device in the scanning device;

derive a measurement correction comprising a scaling factor to apply to measurements of the X-ray image based on the 3-D surface scan and the known spatial relationship between the X-ray imaging device and the 3-D surface scanning device, the measurement correction accounting for at least one of: an orientation of the patient with respect to a detector plate used to capture the X-ray image when the X-ray image was captured, a first distance between the patient and the detector plate, or a second distance between the patient and the X-ray source used to generate the X-ray image when the X-ray image was captured; and determine a corrected measurement of the anatomical part based on the measurement correction and a measurement taken from the X-ray image, wherein to derive the measurement correction comprises to:

obtain a statistical shape model (SSM) comprising data representative of external patient anatomy and data representative of one or more of internal anatomy or one or more internal anatomical landmarks;

fit the data representative of external patient anatomy of the SSM to the 3-D surface scan to generate an SSM instance comprising modified data representative of the one or more of the internal anatomy or the one or more internal anatomical landmarks; and derive the measurement correction based on the modified data representative of the one or more of the internal anatomy or the one or more internal anatomical landmarks.

2. The system of claim 1, wherein to derive the measurement correction comprises to:

derive at least one of the first distance or the second distance based on the 3-D surface scan;

obtain a third distance between the X-ray source and the detector plate; and calculate the scaling factor based on the at least one of the first distance or the second distance and the third distance.

3. The system of claim 2, wherein to derive the at least one of the first distance or the second distance based on the 3-D surface scan comprises to:

locate a region in the 3-D surface scan; and calculate the at least one of the first distance or the second distance as between the region and at least one of the X-ray source and the detector plate.

4. The system of claim 3, wherein the region comprises an anatomical landmark.

5. The system of claim 2, wherein to derive the at least one of the first distance or the second distance based on the 3-D surface scan comprises to:

calculate the at least one of the first distance or the second distance as between a region of the modified data representative of the one or more of the internal anatomy or the one or more internal anatomical landmarks and at least one of the X-ray source and the detector plate.

6. The system of claim 5, wherein the region comprises an anatomical landmark.

7. The system of claim 1, wherein to derive the measurement correction comprises to:

determine the orientation based on the 3-D surface scan.

8. The system of claim 1, wherein to derive the measurement correction comprises to:

determine the orientation based on the modified data representative of the one or more of the internal anatomy or the one or more internal anatomical landmarks.

9. The system of claim 1, wherein the at least one processor is configured to cause the system to:

generate a patient-specific surgical design based on the corrected measurement.

10. The system of claim 9, wherein the at least one processor is configured to cause the system to:

cause manufacture of the patient-specific surgical design using additive manufacturing.

11. A method for calibrating an X-ray image, the method comprising:

receiving an X-ray image of an anatomical part of a patient, wherein the X-ray image is obtained by an X-ray imaging device including an X-ray source;

receiving a 3-D surface scan of a surface of a portion of the patient where the anatomical part is located, wherein the 3-D surface scan is obtained by a 3-D surface scanning device, wherein the X-ray imaging device and the 3-D surface scanning device are part of a scanning device and have a known spatial relationship between the X-ray imaging device and the 3-D surface scanning device in the scanning device;

deriving a measurement correction comprising a scaling factor to apply to measurements of the X-ray image based on the 3-D surface scan and the known spatial relationship between the X-ray imaging device and the 3-D surface scanning device, the measurement correction accounting for at least one of: an orientation of the patient with respect to a detector plate used to capture the X-ray image when the X-ray image was captured, a first distance between the patient and the detector plate, or a second distance between the patient and the X-ray source used to generate the X-ray image when the X-ray image was captured; and determining a corrected measurement of the anatomical part based on the measurement correction and a measurement taken from the X-ray image, wherein deriving the measurement correction comprises:

obtaining a statistical shape model (SSM) comprising data representative of external patient anatomy and data representative of one or more of internal anatomy or one or more internal anatomical landmarks;

fitting the data representative of external patient anatomy of the SSM to the 3-D surface scan to generate an SSM instance comprising modified data representative of the one or more of the internal anatomy or the one or more internal anatomical landmarks; and deriving the measurement correction based on the modified data representative of the one or more of the internal anatomy or the one or more internal anatomical landmarks.

12. The method of claim 11, wherein deriving the measurement correction comprises:

deriving at least one of the first distance or the second distance based on the 3-D surface scan;

obtaining a third distance between the X-ray source and the detector plate; and calculating the scaling factor based on the at least one of the first distance or the second distance and the third distance.

13. The method of claim 12, wherein deriving the at least one of the first distance or the second distance based on the 3-D surface scan comprises:

locating a region in the 3-D surface scan; and calculating the at least one of the first distance or the second distance as between the region and at least one of the X-ray source and the detector plate.

14. The method of claim 13, wherein the region comprises an anatomical landmark.

15. The method of claim 12, wherein deriving the at least one of the first distance or the second distance based on the 3-D surface scan comprises:

calculating the at least one of the first distance or the second distance as between a region of the modified data representative of the one or more of the internal anatomy or the one or more internal anatomical landmarks and at least one of the X-ray source and the detector plate.

16. The method of claim 15, wherein the region comprises an anatomical landmark.

17. The method of claim 11, wherein deriving the measurement correction comprises:

determining the orientation based on the 3-D surface scan.

18. The method of claim 11, wherein deriving the measurement correction comprises:

determining the orientation based on the modified data representative of the one or more of the internal anatomy or the one or more internal anatomical landmarks.

19. The method of claim 11, further comprising:

generating a patient-specific surgical design based on the corrected measurement.

20. The method of claim 19, further comprising:

causing manufacture of the patient-specific surgical design using additive manufacturing.

21. A non-transitory computer readable medium storing instructions, that when executed by a system, cause the system to perform a method for calibrating an X-ray image, the method comprising:

receiving an X-ray image of an anatomical part of a patient, wherein the X-ray image is obtained by an X-ray imaging device including an X-ray source;

receiving a 3-D surface scan of a surface of a portion of the patient where the anatomical part is located, wherein the 3-D surface scan is obtained by a 3-D surface scanning device, wherein the X-ray imaging device and the 3-D surface scanning device are part of a scanning device and have a known spatial relationship between the X-ray imaging device and the 3-D surface scanning device in the scanning device;

deriving a measurement correction comprising a scaling factor to apply to measurements of the X-ray image based on the 3-D surface scan and the known spatial relationship between the X-ray imaging device and the 3-D surface scanning device, the measurement correction accounting for at least one of: an orientation of the patient with respect to a detector plate used to capture the X-ray image when the X-ray image was captured, a first distance between the patient and the detector plate, or a second distance between the patient and the X-ray source used to generate the X-ray image when the X-ray image was captured; and determining a corrected measurement of the anatomical part based on the measurement correction and a measurement taken from the X-ray image, wherein deriving the measurement correction comprises:

obtaining a statistical shape model (SSM) comprising data representative of external patient anatomy and data representative of one or more of internal anatomy or one or more internal anatomical landmarks;

fitting the data representative of external patient anatomy of the SSM to the 3-D surface scan to generate an SSM instance comprising modified data representative of the one or more of the internal anatomy or the one or more internal anatomical landmarks; and deriving the measurement correction based on the modified data representative of the one or more of the internal anatomy or the one or more internal anatomical landmarks.

* * * * *